(12) United States Patent
Bjorklund et al.

(10) Patent No.: US 11,911,623 B2
(45) Date of Patent: Feb. 27, 2024

(54) IMPLANTABLE MEDICAL ELECTRODE ASSEMBLIES, DEVICES, SYSTEMS, KITS, AND METHODS

(71) Applicant: Medtronic, Inc., Minneapolis, MN (US)

(72) Inventors: Vicki L. Bjorklund, Shoreview, MN (US); Xin Chen, Circle Pines, MN (US); William J. Clemens, Fridley, MN (US); Lilian Kornet, Berg en Terblijt (NL); Jean Rutten, Gulpen (NL); Berthold Stegemann, Kassel (DE); Zhongping Yang, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 417 days.

(21) Appl. No.: 16/290,112

(22) Filed: Mar. 1, 2019

(65) Prior Publication Data
US 2019/0269929 A1 Sep. 5, 2019

Related U.S. Application Data

(60) Provisional application No. 62/637,739, filed on Mar. 2, 2018.

(51) Int. Cl.
*A61N 1/368* (2006.01)
*A61N 1/05* (2006.01)
(Continued)

(52) U.S. Cl.
CPC .......... *A61N 1/36843* (2017.08); *A61B 5/287* (2021.01); *A61B 90/39* (2016.02);
(Continued)

(58) Field of Classification Search
None
See application file for complete search history.

(56) References Cited

U.S. PATENT DOCUMENTS

| 3,814,104 A | 6/1974 | Irnich et al. |
| 3,943,936 A | 3/1976 | Rasor et al. |

(Continued)

FOREIGN PATENT DOCUMENTS

| CN | 106994207 A | 8/2017 |
| WO | 2002022202 A2 | 3/2002 |
| WO | 2006118865 A2 | 11/2006 |

OTHER PUBLICATIONS

Definition of "on" from The American Heritage(R) Dictionary of the English Language, 2016 (Year: 2016).*
(Continued)

*Primary Examiner* — Carl H Layno
*Assistant Examiner* — Manolis Pahakis
(74) *Attorney, Agent, or Firm* — Mueting Raasch Group

(57) ABSTRACT

A method, system and device for implanting an electrode assembly of an implantable medical device in a patient's heart. Positioning one or more radiopaque markers in a coronary sinus of the patient's heart. Positioning, by using the one or more positioned radiopaque markers as a fluoroscopic visual reference, a distal tip of a delivery catheter within a right atrium of the patient's heart so that a distal opening of a lumen of the catheter is against a septal wall of the heart at a location between the ostium of the coronary sinus and the A-V nodal area of the right atrium, and so that the tip of the catheter is generally directed toward a left ventricle of the patient's heart. Advancing the electrode assembly through the lumen of the catheter and into the septal wall.

8 Claims, 13 Drawing Sheets

(51) Int. Cl.
  *A61B 90/00* (2016.01)
  *A61N 1/375* (2006.01)
  *A61B 5/287* (2021.01)
  *A61N 1/362* (2006.01)

(52) U.S. Cl.
  CPC ............ *A61N 1/059* (2013.01); *A61N 1/0573* (2013.01); *A61N 1/0592* (2013.01); *A61N 1/37512* (2017.08); *A61B 2090/3966* (2016.02); *A61B 2090/3987* (2016.02); *A61N 1/368* (2013.01); *A61N 1/3627* (2013.01)

(56) References Cited

U.S. PATENT DOCUMENTS

| | | | |
|---|---|---|---|
| 4,103,690 A | 8/1978 | Harris | |
| 4,142,530 A | 3/1979 | Wittkampf | |
| 4,269,198 A | 5/1981 | Stokes | |
| 4,280,512 A | 7/1981 | Karr et al. | |
| 4,355,642 A | 10/1982 | Alferness | |
| 4,628,943 A * | 12/1986 | Miller | A61N 1/056 607/131 |
| 4,679,572 A * | 7/1987 | Baker, Jr. | A61N 1/0573 607/131 |
| 4,858,623 A | 8/1989 | Bradshaw et al. | |
| 4,936,823 A | 6/1990 | Colvin | |
| 5,193,540 A | 3/1993 | Schulman et al. | |
| 5,411,535 A | 5/1995 | Fujii et al. | |
| 5,487,758 A * | 1/1996 | Hoegnelid | A61N 1/0573 607/123 |
| 5,573,540 A | 11/1996 | Yoon | |
| 5,683,447 A | 11/1997 | Bush et al. | |
| 5,728,140 A | 3/1998 | Salo et al. | |
| 6,007,558 A | 12/1999 | Ravenscroft et al. | |
| 6,151,525 A | 11/2000 | Soykan et al. | |
| 6,212,434 B1 * | 4/2001 | Scheiner | A61N 1/0563 607/123 |
| 6,240,322 B1 | 5/2001 | Peterfeso et al. | |
| 6,286,512 B1 | 9/2001 | Loeb et al. | |
| 6,409,674 B1 | 6/2002 | Brockway et al. | |
| 6,501,994 B1 * | 12/2002 | Janke | A61N 1/0573 607/127 |
| 6,507,756 B1 * | 1/2003 | Heynen | A61N 1/3627 607/25 |
| 6,575,967 B1 | 6/2003 | Leveen et al. | |
| 6,783,499 B2 | 8/2004 | Schwartz | |
| 6,915,149 B2 | 7/2005 | Ben-Haim | |
| 6,978,178 B2 | 12/2005 | Sommer et al. | |
| 7,290,743 B2 | 11/2007 | Nowack | |
| 7,305,270 B1 * | 12/2007 | Kroll | A61N 1/3702 600/374 |
| 7,369,901 B1 * | 5/2008 | Morgan | A61N 1/059 600/377 |
| 7,418,298 B2 | 8/2008 | Shiroff et al. | |
| 8,353,940 B2 | 1/2013 | Benderev | |
| 8,670,824 B2 | 3/2014 | Anderson et al. | |
| 8,938,294 B2 | 1/2015 | Anderson et al. | |
| 9,731,138 B1 * | 8/2017 | Stadler | A61N 1/37288 |
| 2001/0044619 A1 * | 11/2001 | Altman | A61N 1/0587 604/539 |
| 2002/0103424 A1 | 8/2002 | Swoyer et al. | |
| 2002/0165589 A1 | 11/2002 | Imran et al. | |
| 2003/0088301 A1 | 5/2003 | King | |
| 2003/0199938 A1 * | 10/2003 | Smits | A61B 5/283 607/27 |
| 2003/0204233 A1 * | 10/2003 | Laske | A61N 1/057 607/127 |
| 2003/0220676 A1 * | 11/2003 | Helland | A61N 1/056 607/122 |
| 2004/0127967 A1 * | 7/2004 | Osypka | A61N 1/059 607/122 |
| 2004/0147973 A1 | 7/2004 | Hauser | |
| 2004/0230281 A1 | 11/2004 | Heil et al. | |
| 2006/0041300 A1 * | 2/2006 | Zhang | A61N 1/0573 607/126 |
| 2006/0084965 A1 | 4/2006 | Young | |
| 2006/0085039 A1 | 4/2006 | Hastings et al. | |
| 2006/0085041 A1 | 4/2006 | Hastings et al. | |
| 2007/0021813 A1 * | 1/2007 | Sommer | A61N 1/0575 607/127 |
| 2007/0150009 A1 * | 6/2007 | Kveen | A61F 2/88 607/9 |
| 2008/0039896 A1 * | 2/2008 | Osypka | A61N 1/056 607/9 |
| 2008/0294229 A1 * | 11/2008 | Friedman | A61N 1/0573 607/127 |
| 2009/0082828 A1 | 3/2009 | Ostroff | |
| 2009/0259272 A1 * | 10/2009 | Reddy | A61N 1/0573 607/28 |
| 2012/0172892 A1 | 7/2012 | Grubac et al. | |
| 2012/0232563 A1 * | 9/2012 | Williams | A61M 25/0147 606/129 |
| 2012/0245665 A1 * | 9/2012 | Friedman | A61N 1/0573 607/127 |
| 2014/0039591 A1 | 2/2014 | Drasler et al. | |
| 2015/0039070 A1 | 2/2015 | Kuhn et al. | |
| 2016/0279423 A1 * | 9/2016 | Kelly | A61M 25/0136 |
| 2016/0361536 A1 * | 12/2016 | Grubac | A61N 1/0573 |
| 2017/0189674 A1 * | 7/2017 | Camps | A61N 1/0563 |
| 2017/0326369 A1 * | 11/2017 | Koop | A61N 1/0573 |
| 2017/0326372 A1 * | 11/2017 | Koop | A61N 1/3756 |
| 2018/0272121 A1 * | 9/2018 | Yankelson | A61N 1/37518 |
| 2019/0083800 A1 * | 3/2019 | Yang | A61N 1/3756 |
| 2019/0083801 A1 * | 3/2019 | Yang | A61N 1/37518 |
| 2019/0111270 A1 * | 4/2019 | Zhou | A61N 1/3956 |
| 2019/0151666 A1 * | 5/2019 | Bonnet | A61N 1/3682 |
| 2019/0290909 A1 * | 9/2019 | Ghosh | A61B 5/282 |
| 2020/0306529 A1 * | 10/2020 | Asleson | A61M 25/0082 |
| 2021/0228892 A1 * | 7/2021 | Kornet | A61N 1/3702 |

OTHER PUBLICATIONS (PCT/US2019/020278) PCT Notification of Transmittal of the International Search Report and the Written Opinion of the International Searching Authority, dated May 15, 2019, 31 pages.

Haqqani et al., "The Implantable Cardioverter-Defibrillator Lead: Principles, Progress and Promises," PACE, vol. 32, Oct. 2009, pp. 1336-1353.

Tjong et al., "Acute and 3-Month Performance of a Communicating Leadless Antitachycardia Pacemaker and Subcutaneous Implantable Defibrillator," JACC: Clinical Electrophysiology, vol. 3, No. 13, Dec. 26, 2017, pp. 1487-1498.

Tjong et al., "The modular cardiac rhythm management system: the Empower leadless pacemaker and the Emblem subcutaneous ICD," Herzschrittmachertherapie + Elektrophysiologie, vol. 29, Oct. 31, 2018, pp. 355-361.

* cited by examiner

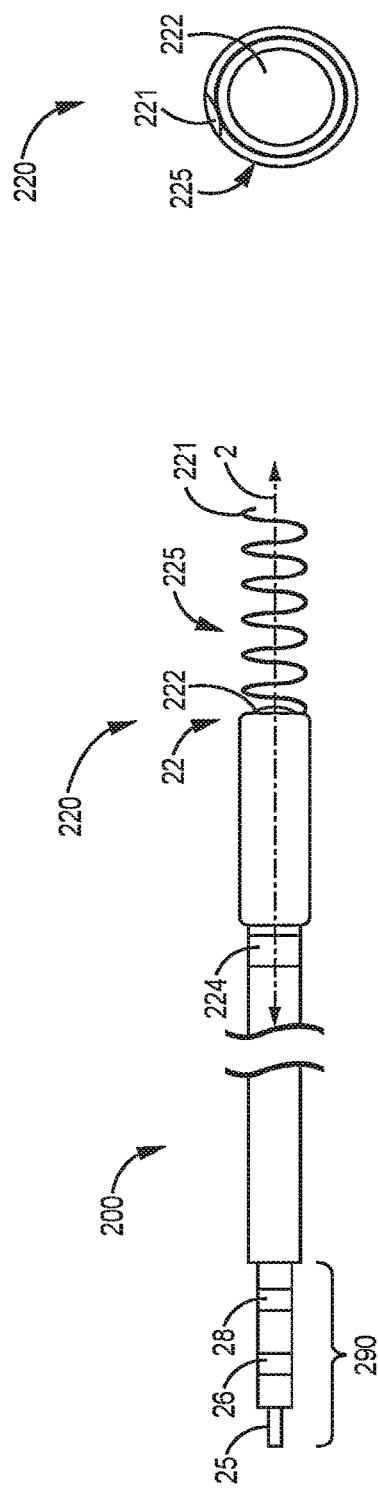
FIG. 2A
FIG. 2B
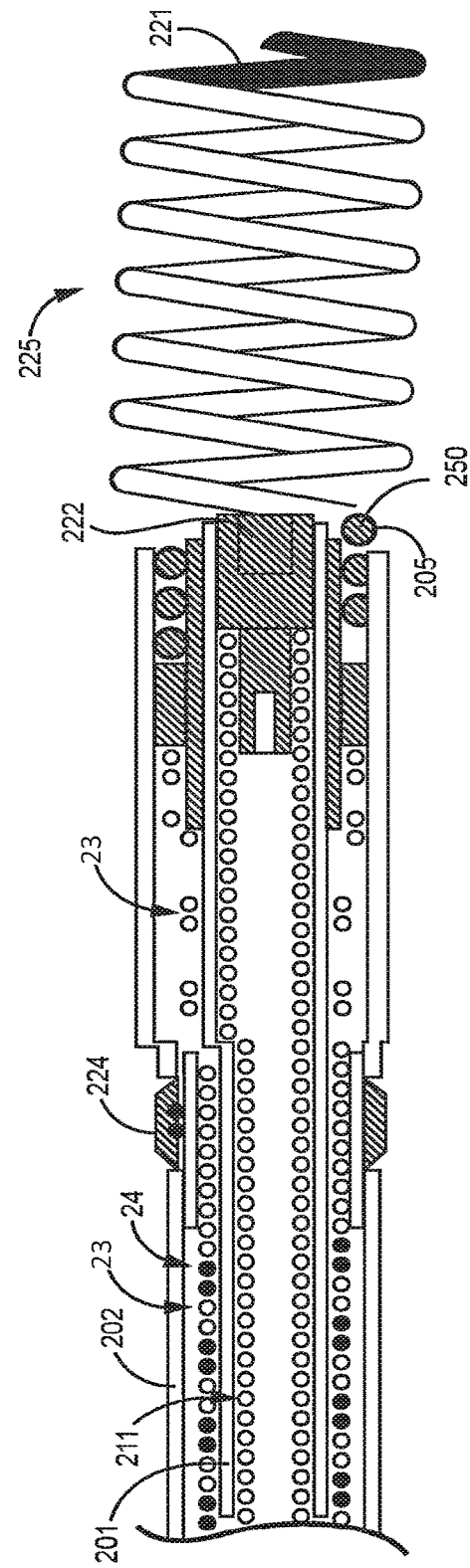
FIG. 2C

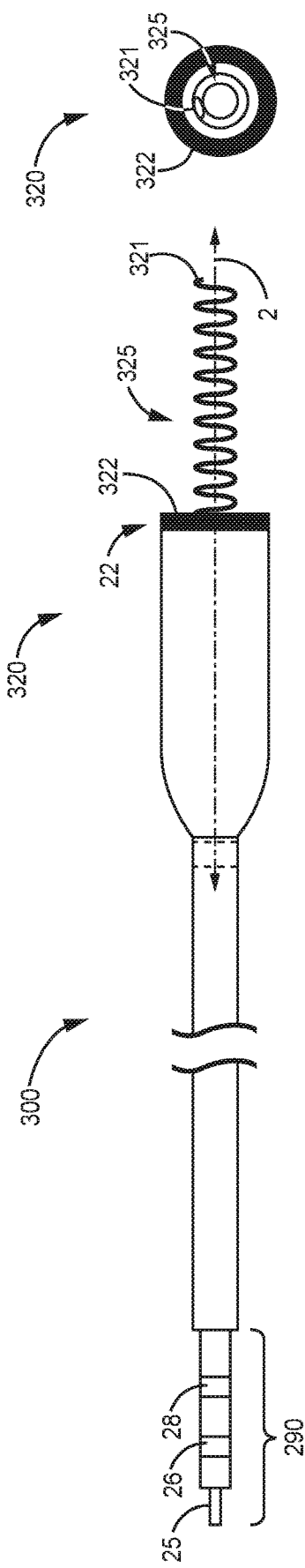
FIG. 3A
FIG. 3B
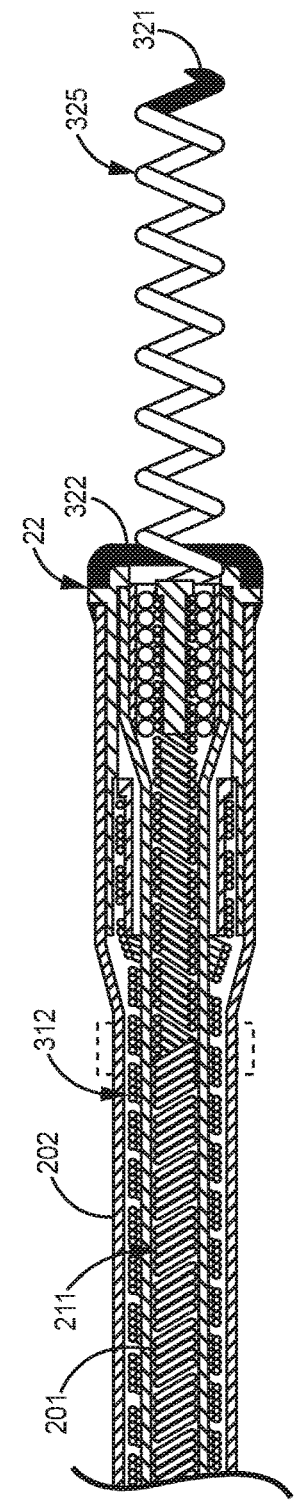
FIG. 3C

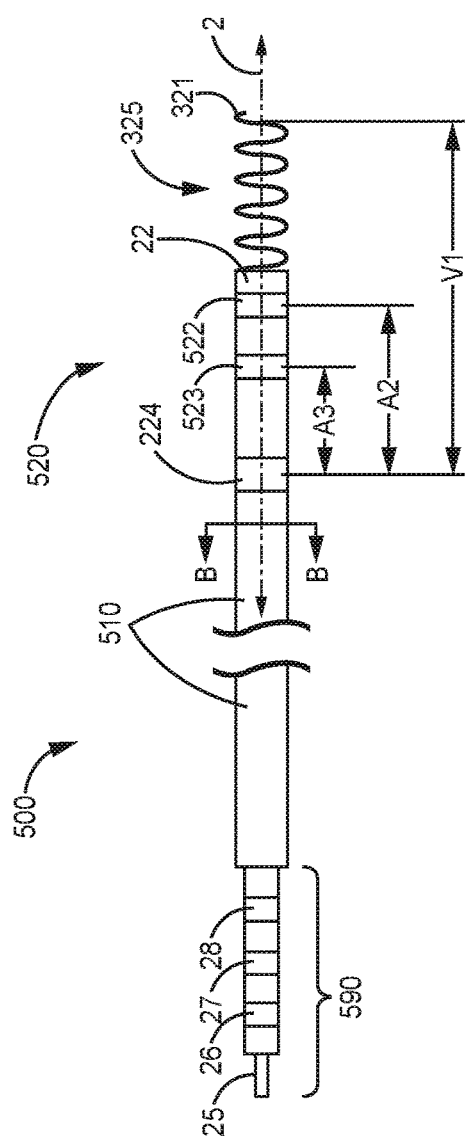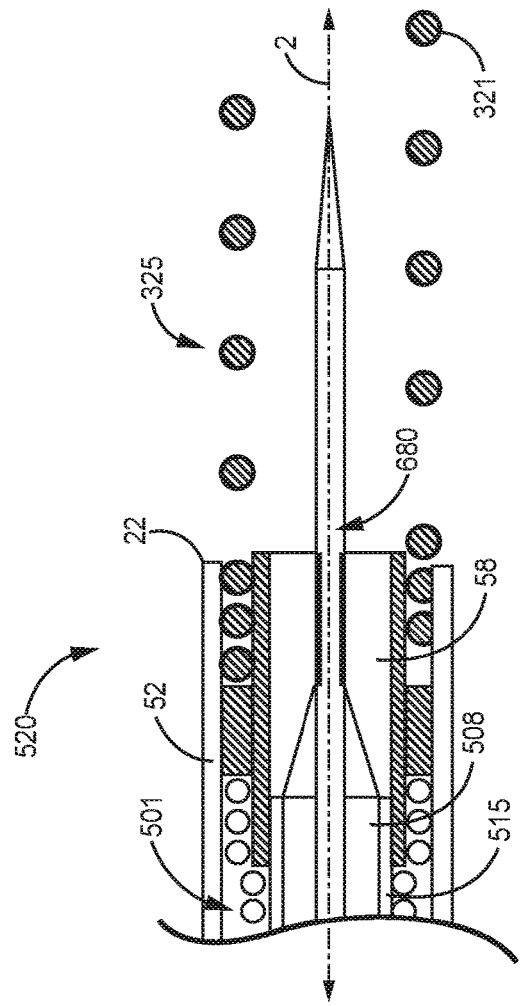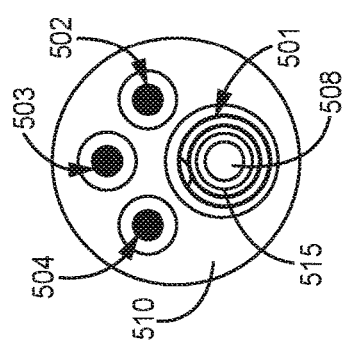
FIG. 5A
FIG. 5B
FIG. 5C

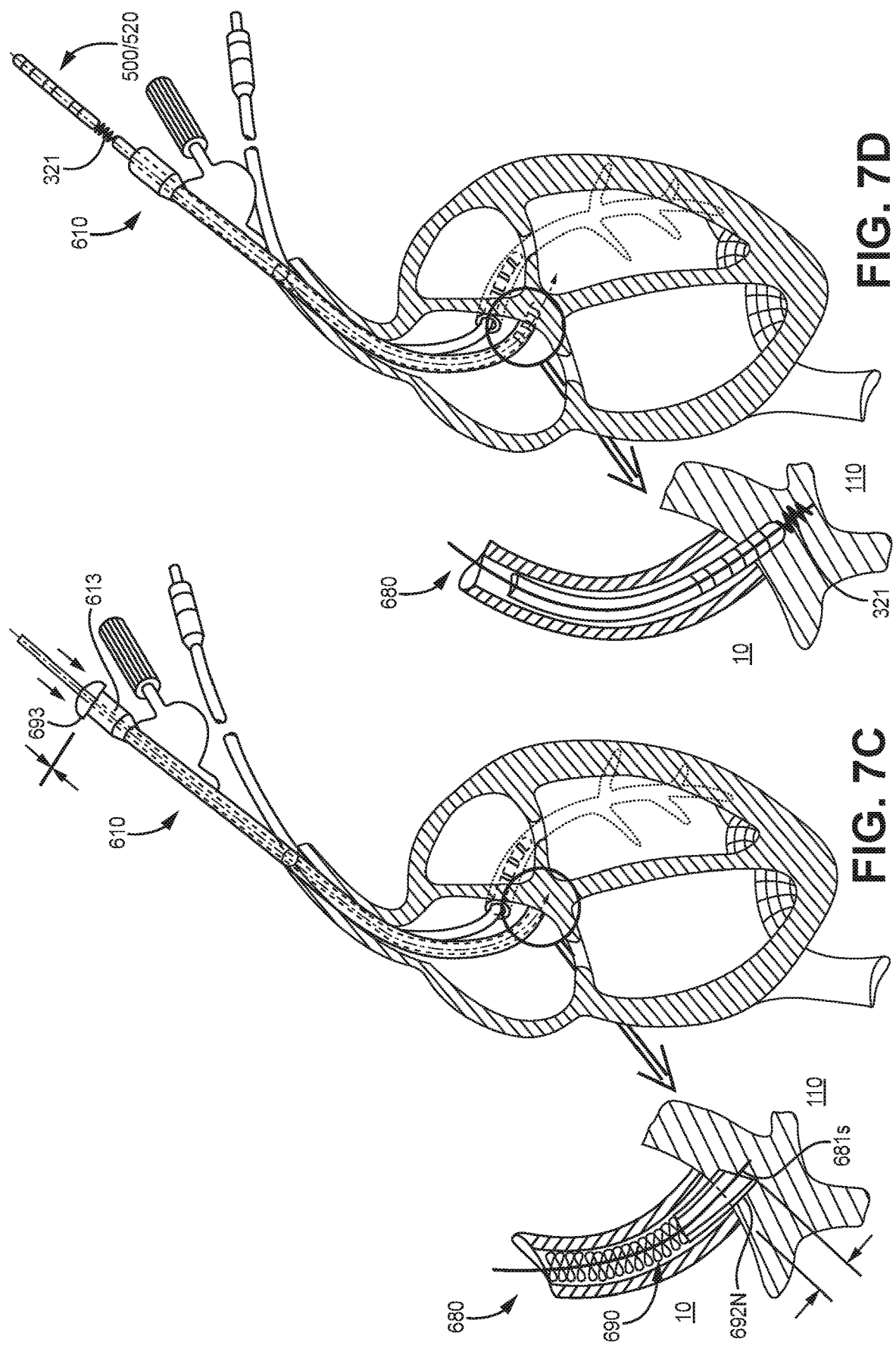

IMPLANTABLE MEDICAL ELECTRODE ASSEMBLIES, DEVICES, SYSTEMS, KITS, AND METHODS

CROSS-REFERENCE TO RELATED APPLICATIONS

This application claims the benefit of U.S. Provisional Application No. 62/637,739 filed on Mar. 2, 2018. The disclosure of the above application is incorporated herein by reference in its entirety.

FIELD OF THE DISCLOSURE

The present disclosure pertains to cardiac pacing, and more particularly to implantable medical electrode assemblies, devices, interventional delivery systems, kits, and associated methods, all for the purpose of providing atrial synchronized left ventricular pacing or trans-septal bi-ventricular cardiac pacing.

BACKGROUND

The activity of a normal, healthy heart involves synchronized contractions of the chambers of the heart that are caused by coordinated electrical activation of portions of the cardiac muscle.

The heartbeat cycle begins with the generation of an electrical impulse by the sinoatrial node of the heart, which is located near the upper portion of the right atrium in proximity to the superior vena cava. This impulse spreads across the atria, stimulating the atrial muscles to contract and force blood into the ventricles. An atrial contraction is manifested as the so-called "P-wave" in an electrocardiographic signal. The electrical impulse conducted through the atrial muscle travels to atrio-ventricular node or A-V node in proximity to the partition wall immediately beside the valve between the right atrium and right ventricle. The A-V node introduces a slight delay in the transmission of the electrical impulse to the ventricles. This A-V delay is typically on the order of 100 milliseconds. After the A-V delay, the electrical impulse is conducted to the ventricles, causing the ventricular contraction which is manifested as the "QRS complex" of an electrocardiographic signal. Subsequent repolarization and relaxation of the ventricular muscles occurs at the end of the cardiac cycle, which is manifested as the "T-wave" portion of an electrocardiographic signal.

For patients in which the above-described conduction of electrical impulses through the cardiac muscle is somehow impaired, a pacemaker can provide an artificial electrical stimulus where no natural electrical impulse is present. Thus, for example, a ventricular pacemaker can function to cause ventricular contractions in patients in which the natural electrical cardiac impulse is, for some reason, not transmitted across the A-V node. It is important, however, that any artificial stimulating pulses be delivered at appropriate times, so that proper synchronization of atrial and ventricular action is maintained. In addition, it is known that electrical impulses being delivered to the cardiac muscle during the repolarization phase at the end of the cardiac cycle can cause the onset of tachyarrhythmias. It is therefore important that the pacemaker be prevented from delivering stimulating pulses during the T-wave.

In order to maintain atrio-ventricular synchrony, and to prevent delivery of pacing pulses at undesirable times, pacemakers are preferably capable of detecting either atrial activity, ventricular activity, or both, as manifested by the P-wave and QRS complex (or more typically the R-wave), respectively, via atrial and ventricular cardiac electrogram signals sensed by the pacemaker.

Pacemakers are generally characterized by which chambers of the heart they are capable of sensing, the chambers to which they deliver pacing stimuli, and their responses, if any, to sensed intrinsic electrical cardiac activity. Some pacemakers deliver pacing stimuli at fixed, regular intervals without regard to naturally occurring cardiac activity. More commonly, however, pacemakers sense electrical cardiac activity in one or both of the chambers of the heart and inhibit or trigger delivery of pacing stimuli to the heart based on the occurrence and recognition of sensed intrinsic electrical events.

The North American Society of Pacing and Electrophysiology (NASPE) and the British Pacing and Electrophysiology Group (BPEG) have adopted a three-letter code which is used to describe the operative modalities of pacemakers. The first letter of the three-letter code designates the chamber or chambers of the heart to which the pacemaker delivers pacing pulses; an "A" in the first position designates atrial pacing, a "V" designates ventricular pacing, and a "D" designates both atrial and ventricular pacing. Similarly, the second letter position designates the chambers of the heart from which the pacemaker senses electrical signals, and this second letter may be either an "A" (atrial sensing), a "V" (ventricular sensing), a "D" (atrial and ventricular sensing), or an "O" (no sensing). The third letter position designates the pacemakers responses to sensed electrical signals. The pacemaker's response may either be to trigger the delivery of pacing pulses based upon sensed electrical cardiac signals (designated by a "T" in the third position), to inhibit the delivery of pacing pulses based upon sensed electrical cardiac signals (designated by an "I" in the third position), or both trigger and inhibit based upon sensed electrical cardiac signals (designated by a "D"). An "O" so in the third position indicates that the pacemaker does not respond to sensed electrical signals. Thus, for example, a "WI" pacemaker delivers pacing stimuli to the ventricle of a patient's heart, senses electrical cardiac activity in the ventricle, and inhibits the delivery of pacing pulses when ventricular signals are sensed. A "DDD" pacemaker, on the other hand, delivers pacing stimuli to both the atrium and ventricle of the patient's heart, senses electrical signals in both the atrium and ventricle, and both triggers and inhibits the delivery of pacing pulses based upon sensed electrical cardiac activity. The delivery of each pacing stimulus by a DDD pacemaker is synchronized with prior sensed or paced events. Other well-known types of pacemakers include AOO, VOO, AAI, VDD, and DVI. Synchronous atrioventricular (AV) cardiac pacing, for example, as delivered from an implanted dual chamber pacemaker device, or a DDD pacemaker provides good clinical outcomes for patients with complete AV block, sick sinus syndrome, and paroxysmal AV block.

Various configurations of implantable dual chamber pacemaker devices are known in the art, but there is still a need for improved device electrode assembly configurations and corresponding interventional delivery systems, kits, and methods.

BRIEF DESCRIPTION OF THE DRAWINGS

The following drawings are illustrative of particular embodiments of the present disclosure and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements.

FIG. 2A is a plan view of an electrode assembly integrated into an elongate implantable medical electrical lead for an implantable medical device, according to some embodiments.

FIG. 2B is a distal end view of the electrode assembly depicted in FIG. 2A.

FIG. 2C is a partial longitudinal cross-section view of medical electrical lead coaxial conductor construction.

FIG. 3A is a plan view of an electrode assembly integrated into an elongate implantable medical electrical lead for an implantable medical device, according to some embodiments.

FIG. 3B is a distal end view of the electrode assembly depicted in FIG. 3A.

FIG. 3C depicts the coaxial construction of the electrode assembly of FIGS. 3A-3B.

FIG. 5A is a plan view of an electrode assembly integrated into an elongate implantable medical electrical lead, according to some additional embodiments.

FIG. 5B is a cross-section view through section line B-B of FIG. 5A, according to some embodiments.

FIG. 5C is a longitudinal cross-section view through the electrode assembly of FIG. 5A, in proximity to a distal end thereof, according to some embodiments.

FIG. 7C is a schematic diagram that depicts creation of a blind bore after positioning the delivery catheter, according to some methods.

FIG. 7D is schematic diagram that depicts a lead electrode assembly advanced into the bore, according to some methods.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives. Embodiments will hereinafter be described in conjunction with the appended drawings wherein like numerals denote like elements. The drawings are not to scale (unless so stated) and are intended for use in conjunction with the explanations in the following detailed description.

Figure 1A:
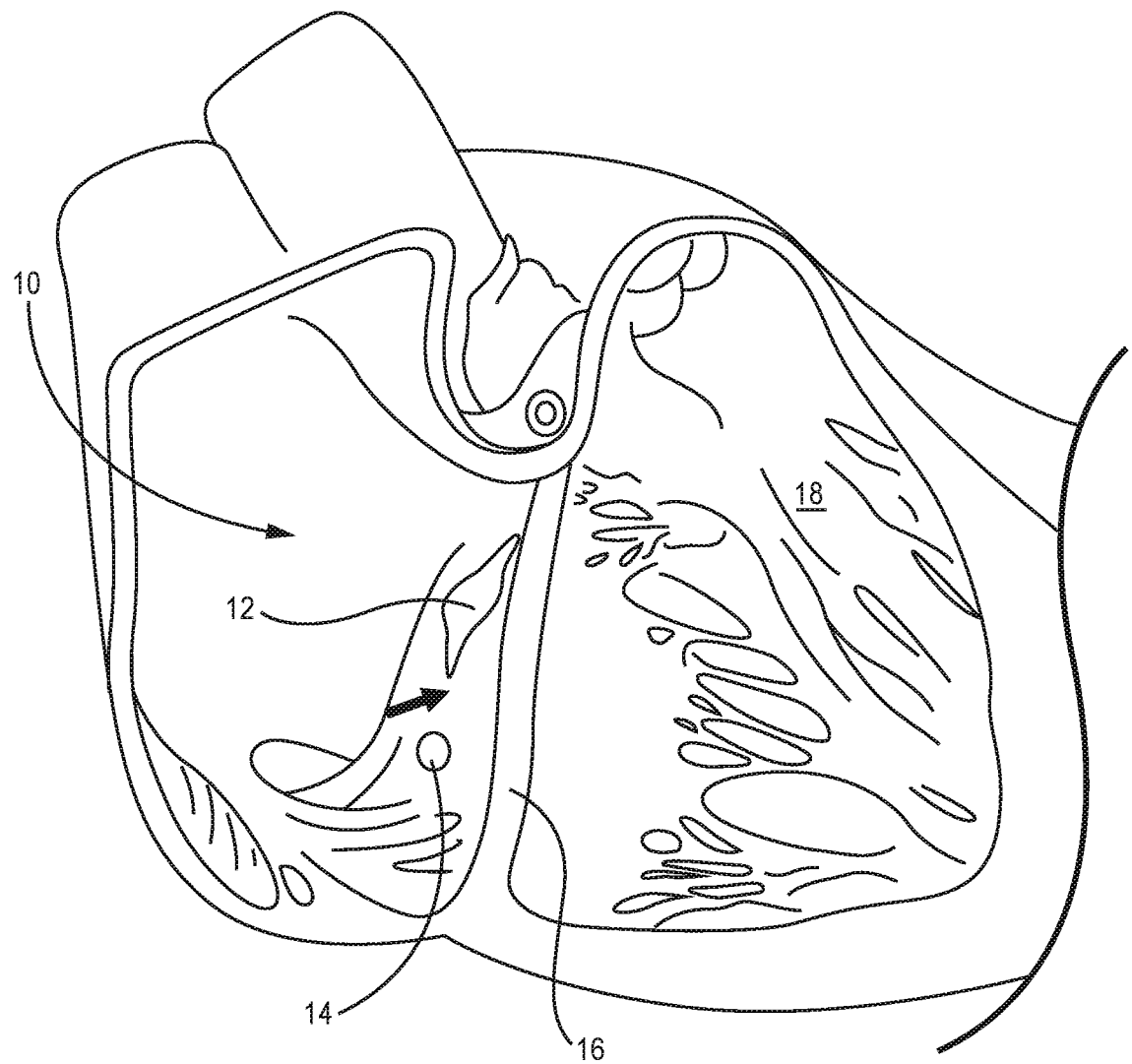
FIG. 1A is a schematic diagram of a right side of a heart having an anterior-lateral wall cut-away to expose the septal wall of the right atrium (RA).
Figure 1B:
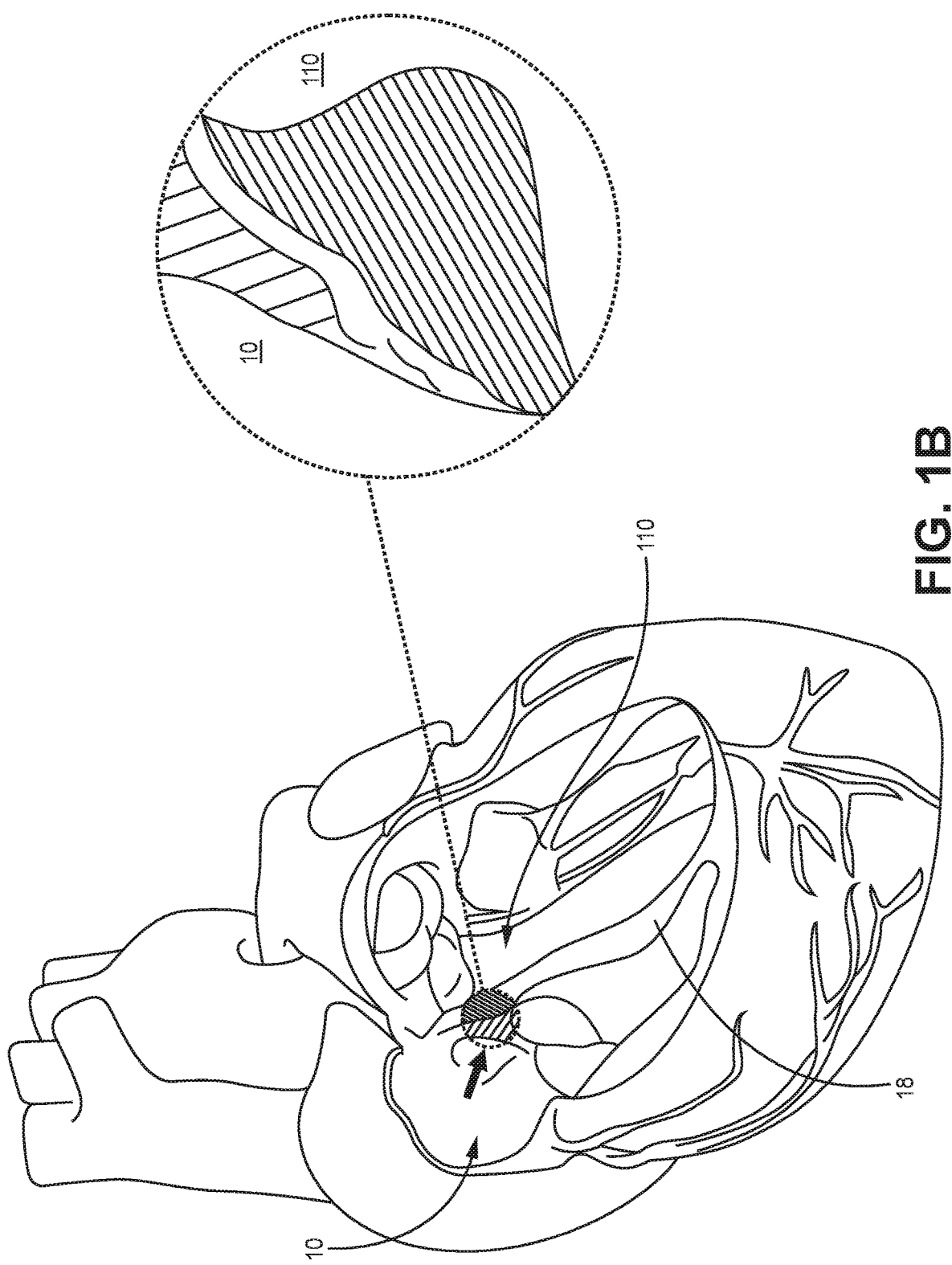
FIG. 1B is a schematic diagram of a heart from a slightly different perspective relative to FIG. 1A with a different area of the heart wall cut-away to expose a cross-section of the septal wall between the RA and the left ventricle (LV).

Conventional dual chamber pacemaker devices provide synchronous pacing through multiple electrode assemblies, for example, an electrode assembly implanted in the right atrium (RA) of a patient's heart and another electrode assembly implanted in the right ventricle (RV) of the patient's heart. Embodiments described herein encompass a single electrode assembly that can be employed in lieu of these two assemblies, preferably to provide synchronous pacing of the RA and the left ventricle (LV). For example, with reference to the schematic diagrams of FIGS. 1A-B, electrode assemblies described herein are configured for implant within a septal wall of the patient's heart, preferably entering the wall from the RA 10, between the Atrioventricular (AV) nodal area 12 of the heart's intrinsic conduction system and the ostium 14 of the coronary sinus (CS), as indicated with the bold-faced arrow in each of FIGS. 1A-B, and passing through a fibrous layer, which extends between right atrial and left ventricular myocardial tissue, so that electrodes of the assembly are positioned to stimulate both the right atrial myocardial tissue and the left ventricular myocardial tissue (indicated with coarse cross-hatching and fine cross-hatching, respectively, in FIG. 1B). FIG. 1A is a schematic diagram of the right side of the heart having an anterior-lateral wall cut-away to expose the septal wall of the RA 10, posterior to the annulus of the tricuspid valve 16, and the intraventricular septum 18 of the RV and the LV 110. The schematic diagram of FIG. 1B shows the heart from a slightly different perspective with a different area of the heart wall cut-away to expose a cross-section of the septal wall between the RA 10 and the LV 110, which is also shown magnified.

Employing a single electrode assembly to deliver atrial synchronized left ventricular pacing (e.g., according to the embodiments described below in conjunction with FIGS. 2A-C, 3A-C and 5A-C) is beneficial in a number of different ways. For example, a single electrode assembly provides more hemodynamically favorable pacing (avoiding interference with the tricuspid valve 16 that could lead to regurgitation, and stimulation of left ventricular myocardial tissue in the high septal wall). A single electrode assembly also reduces pacemaker device complexity leading to improved reliability. Moreover, the bulk of implanted hardware is reduced thereby resulting in improved patient comfort and a reduced probability of complications.

The leads as illustrated in FIGS. 2A-C, 3A-C and 5A-C may also be employed to deliver alternate pacing therapies. For example, the lead may also be employed to deliver trans-septal pacing to stimulate both left and right branches of the Purkinje fibers to provide bi-ventricular stimulation.

FIG. 2A is a plan view of an electrode assembly 220 integrated into an elongate implantable medical electrical lead 200 for an implantable medical device, according to some embodiments FIG. 2B shows a distal end view of electrode assembly 220. FIGS. 2A-B illustrate electrode assembly 220 including a substantially cylindrical body extending distally from a distal length of lead 200 and defining a longitudinal axis 2 of assembly 220, and a fixation member 225 in the form of a helix extending distally from a distal end 22 of the body and along axis 2, for example, being coupled to the body in proximity to distal end 22 and having a pitch of 0.5 to 1.5 mm, with one preferred pitch being 1.0 mm. According to the illustrated embodiment, a first, distal-most cathode electrode 221 of assembly 220 is formed on fixation member 225, for example, at a distal end thereof; however, in alternate embodiments, first cathode electrode 221 may be located along a length of fixation member 225 that is proximal to the distal end thereof. In this embodiment, an entirety of the second cathode electrode 222 extends within an inner perimeter of the fixation member 225. Those skilled in the art will understand that the distal end of fixation member 225 is sharpened to pierce myocardial tissue, for example, of the above-described septal wall, so that fixation member 225 can be screwed into the tissue to secure electrode assembly 220 to the septal wall. In one preferred embodiment, fixation member 225, in order to reach left ventricular myocardial tissue, as described above, extends over a length in a range from 6 mm to 8 mm. In one or more other preferred embodiments, fixation member 225 extends over a length in a range from 5 mm to 15 mm or a range of 5-20 mm. Fixation members of differing lengths may be beneficial to adapt the lead to hearts of varying sizes or to optimize the lead for trans-septal pacing, with longer lengths within the defined ranges particularly beneficial in conjunction with trans-septal pacing.

FIGS. 2A-B further illustrate assembly 220 including a second, proximal-most cathode electrode 222 formed on distal end 22 of the substantially cylindrical body and located on longitudinal axis 2, wherein an entirety of second cathode electrode 222 is within an inner perimeter of fixation member 225. According to an exemplary embodiment, second cathode electrode 222 has an active surface area for stimulating contact with myocardial tissue of about 0.003 inches squared. In the exemplary embodiment, a diameter of the active surface area of second cathode electrode 222 may be up to about 0.08 inch squared. In one preferred embodiment, an inner diameter of fixation member 225 may be 0.08 inch, and an outer diameter of fixation member 225 may be 0.1 inch. In other preferred embodiments, the inner diameter may be from 0.06 inch to 0.12 inch and the outer diameter may correspondingly be from 0.08 to 0.14 inch. With further reference to FIG. 2A, electrode assembly 220 further includes an optional anode electrode 224, for example, being mounted around the distal length of lead 200, proximal to second cathode electrode 222. According to the illustrated embodiment, each of cathode electrodes 221, 222 may function with anode electrode 224 for bipolar pacing and sensing. According to some embodiments, a surface area of anode electrode 224 may be at least four times greater than a surface area of each of cathode electrodes 221, 222.

FIG. 2C is a partial longitudinal cross-section view of lead 200 to illustrate an exemplary construction thereof. FIG. 2C shows a coaxial conductor construction familiar to those skilled in the art. With reference to FIG. 2C in conjunction with FIG. 2A, an inner conductor 211 is shown as a coil extending within a sleeve of inner insulation 201 and along a length of lead 200 to mechanically and electrically couple (e.g. via crimping, swaging, and/or welding methods known in the art) second cathode electrode 222 to a contact ring 26 of a proximal terminal connector 290. A pair of outer conductors 23, 24 are shown as a multi-conductor coil extending within a sleeve of outer insulation 202 to mechanically and electrically couple (e.g. via crimping, swaging, and/or welding methods known in the art) first cathode electrode 221 to a connector pin 25 of connector 290 and anode electrode 224 to another contact ring 28 of connector 290. According to an exemplary embodiment, sleeves of inner and outer insulation 201, 202 are formed of extruded medical grade silicone rubber or polyurethane of a combination thereof; and each of conductors 211, 23, 24 are formed from wires of the well-known medical grade alloy MP35N, wherein conductors 23, 24 are isolated from one another by insulative coatings or jackets of a medical grade polymer extending thereabout, for example, Si Polyimide or a fluoropolymer. FIG. 2C further illustrates fixation member 225 formed by a conductive wire 250 extending within an insulative coating or jacket 205. Insulative coating or jacket 205 extends along a length of wire proximal to the exposed portion of wire 250 that forms first cathode electrode 221 to electrically isolate first cathode electrode 221 from second cathode electrode 222. First cathode electrode 221 may have an active surface area for stimulating contact with myocardial tissue of about 0.0045 inches squared. According to the illustrated embodiment, the exposed portion forming first cathode electrode 221 is located at the distal end of fixation member 223 and extends over about one half of a turn of the helix. According to an exemplary embodiment, conductive wire 250 is formed from 90/10 or 70/30 Pt/1R, and insulative coating or jacket 205 from Parylene.

FIG. 3A is a plan view of an electrode assembly 320 integrated into an elongate implantable medical electrical lead 300 for an implantable medical device, according to some alternate embodiments; and FIG. 3B is a distal end view of electrode assembly 320. Like assembly 220, electrode assembly 320 includes the substantially cylindrical body defining longitudinal axis 2, which extends from a distal length of lead 300, and a fixation member 325 in the form of a helix extending distally from the body and along axis 2, wherein a first, distal-most cathode electrode 321 of assembly 320 is formed on fixation member 325, for example, at a distal end thereof. FIGS. 3A-B further illustrate assembly 320 including a second, proximal-most cathode electrode 322 formed on distal end 22 of the substantially cylindrical body, so that an entirety of second cathode electrode 322 is located outside an outer perimeter of fixation member 325.

According to an exemplary embodiment, second cathode electrode 322 has an active surface area of about 0.0142 inches squared, an outer diameter of second cathode electrode 322 is 0.116 inch, an inner diameter of second cathode electrode 322 is 0.061 inch. In this embodiment, an inner diameter of fixation member 325 is 0.032 inch and an outer diameter of fixation member 325 is 0.057 inch. In other preferred embodiments, the outer diameter of the second cathode electrode 322 may be from 0.1 inch to 0.15 inch, the inner diameter of the second cathode electrode 322 may correspondingly be from 0.05 inch to 0.1 inch, the inner diameter of fixation member 325 may correspondingly be from may be from 0.02 inch to 0.05 inch and the outer diameter of fixation member 325 may correspondingly be from 0.04 to 0.08 inch, with dimensions chosen such that an entirety of second cathode electrode 322 is located outside an outer perimeter of fixation member 325. Fixation member 325 may be constructed like fixation member 225, having a corresponding length and wherein the exposed portion of member 325 extends over about one half turn to form first, distal-most cathode electrode 321. According to one or more embodiments, an active surface area of first cathode electrode 321 is about 0.0022 inches squared. Again, fixation members of differing lengths may be beneficial to adapt the lead to hearts of varying sizes or to optimize the lead for trans-septal pacing.

FIG. 3C is a partial longitudinal cross-section view of lead 300 to illustrate an exemplary construction thereof, which is similar to the coaxial construction described above except that a single conductor outer coil 312 is shown in lieu of the multi-conductor outer coil for the embodiment that does not include an anode electrode. According to embodiments without the anode electrode, cathode electrodes 321, 322 provide unipolar pacing and sensing. However, dashed lines in FIGS. 3A and 3C indicate the location of optional anode electrode for electrode assembly 320, which may be similar to anode electrode 224 described for assembly 220; and it may be appreciated that the multi-conductor coil of FIG. 2C may be employed for the construction of an alternate embodiment of lead 300 that includes the anode electrode. Furthermore, FIG. 3A illustrates lead 300 including connector 290, which is suitable for inclusion of the optional anode electrode.

Figure 4A:
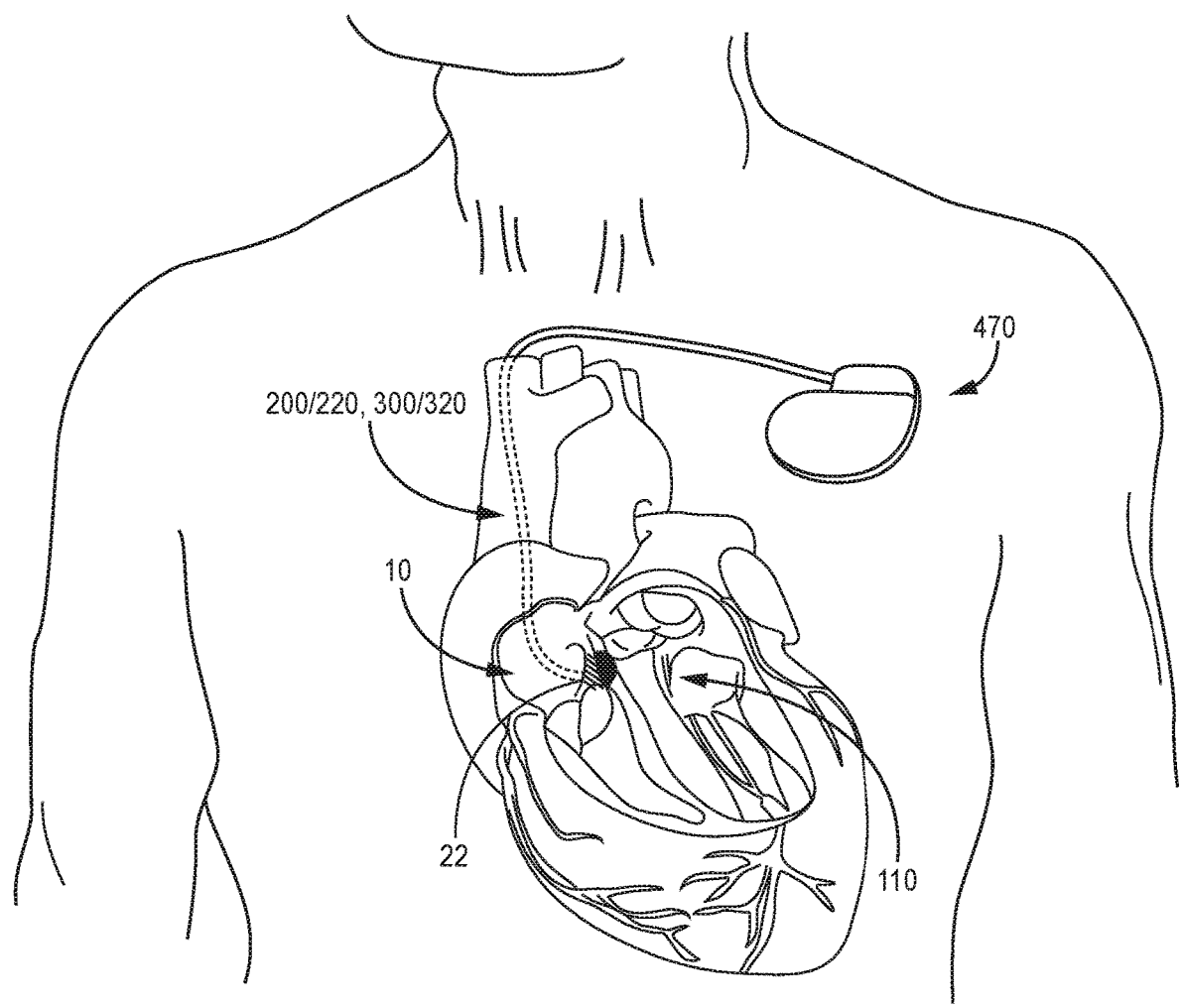
FIG. 4A is a schematic diagram showing a pulse generator implanted in a pectoral pocket of a patient, wherein either of the above-referenced electrode assemblies extends therefrom with distal end against the wall in the RA.

FIGS. 2A-C and 3A-C show the active surface areas of each of second, proximal cathode electrodes 222, 322 facing distally along axis 2 so that when each fixation member 225, 325 secures the corresponding electrode assembly 220, 320 to the septal wall with distal end 22 against the wall in RA 10, for example as illustrated in FIG. 4A, the active surface of each second cathode electrode 222, 322 will be in intimate contact with myocardial tissue of the RA 10 for pacing stimulation thereof. The position of each second cathode electrode 222, 322 relative to the corresponding fixation member perimeters in each embodiment, whether inside the inner perimeter or outside the outer perimeter, may assure that the active surface area of each makes the intimate contact with atrial myocardial tissue that has not suffered acute injury from the piercing of fixation member 225, 325. With further reference to FIGS. 2A and 3A in conjunction with FIG. 4A, proximal terminal connector 290 is configured to connect lead electrode assembly 200/220, 300/320 to a pulse generator 470, by means well known to those skilled in the art, thereby forming an implantable medical device suitable for the above-described synchronous cardiac pacing.

Figure 5E:
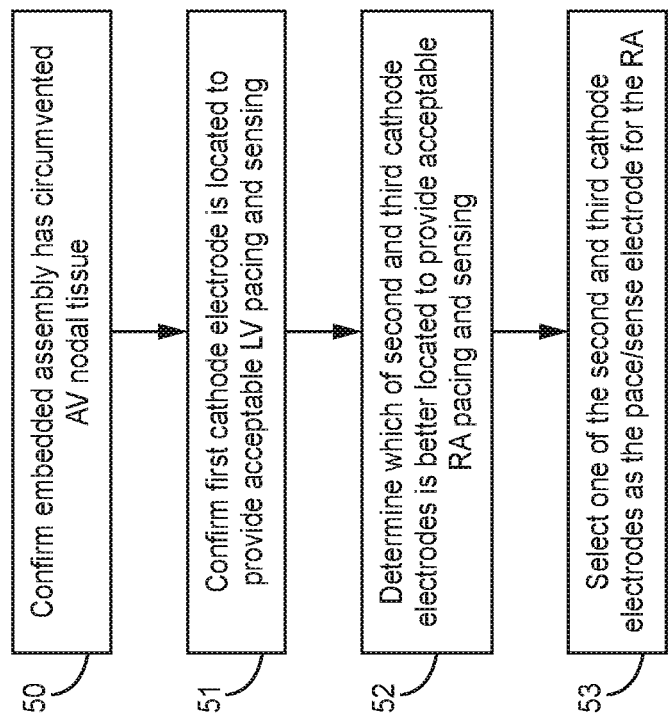
FIG. 5E is a flow chart that outlines an exemplary method for using the embedded electrode assembly of FIG. 5D.
Figure 5D:
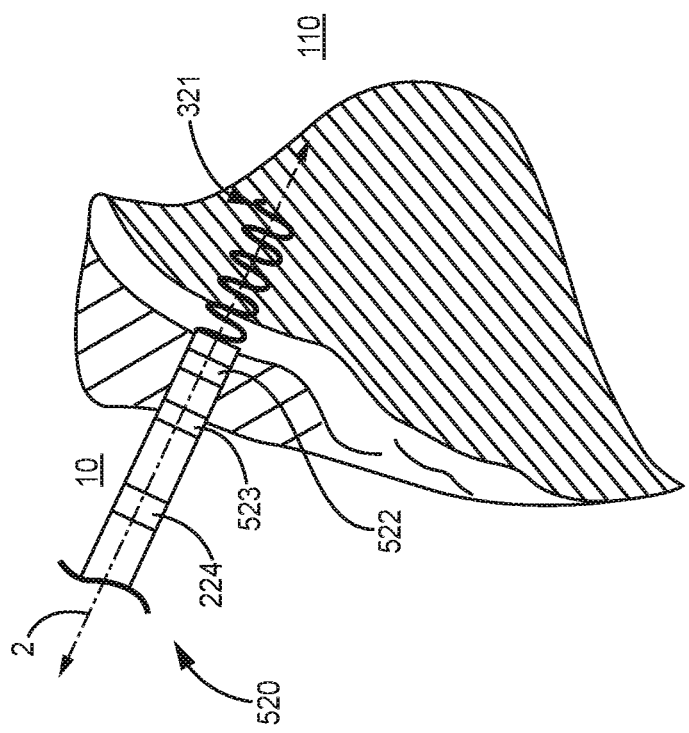
FIG. 5D is a schematic diagram depicting the electrode assembly of FIG. 5A implanted within a blind bore formed in the septal, according to some methods.
Figure 5F:
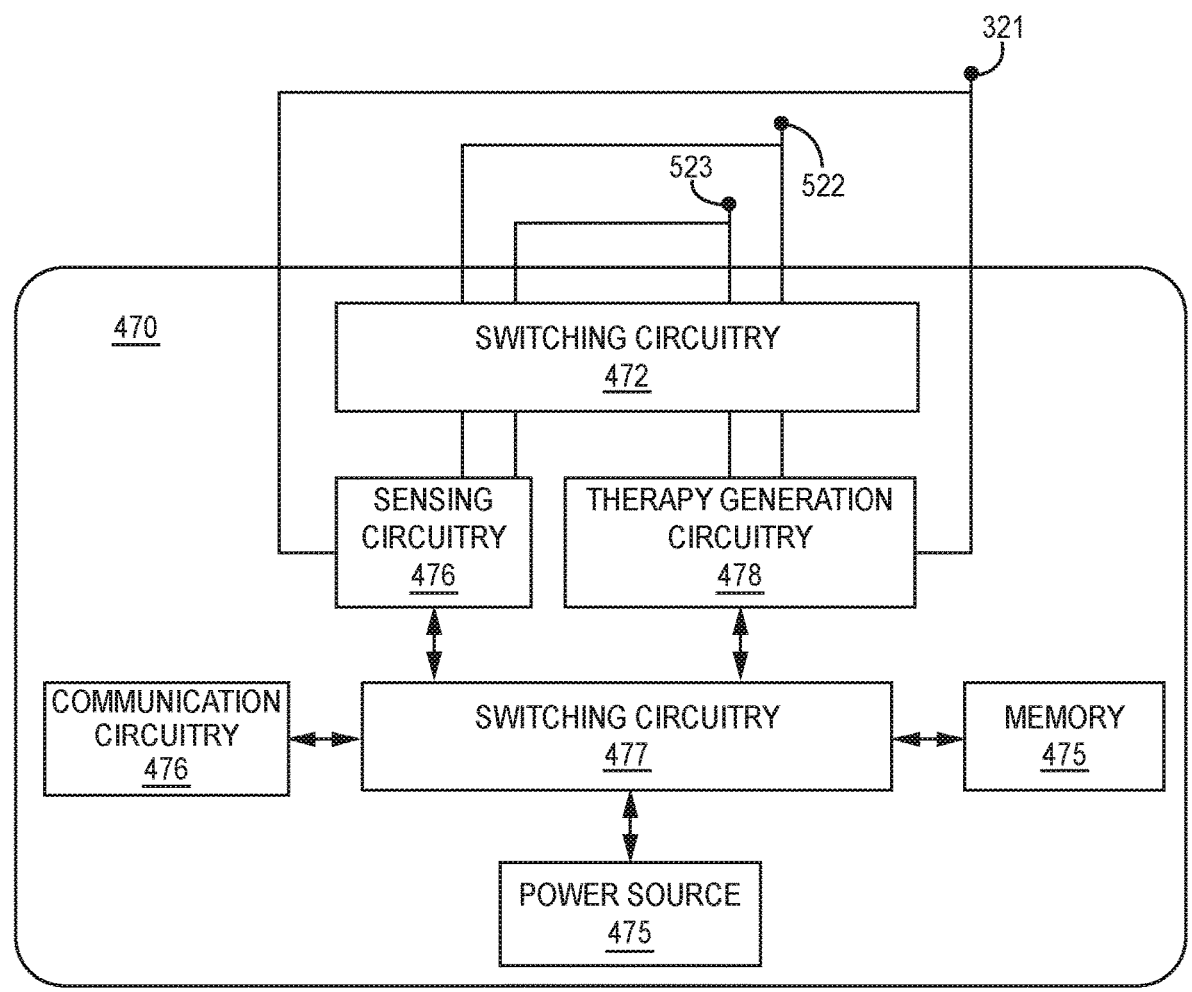
FIG. 5F is a functional block diagram describing an exemplary pulse generator, according to some embodiments presented herein.

FIG. 4A is a schematic showing pulse generator 470 implanted in a pectoral pocket of a patient and lead electrode assembly 200/220, 300/320 extending therefrom and, transvenously, into the RA 10 of the patient's heart where assembly 200/220, 300/320 is secured to the septal wall between the RA 10 and the LV 110. Conventional methods known to those skilled in the art may be employed to implant lead electrode assembly 200/220, 300/320 in the heart prior to connecting lead electrode assembly 200/220, 300/320 to pulse generator 470. However, methods described below in conjunction with FIGS. 6 and 7A may alternately be employed to implant lead electrode assemblies 200/220, 300/320. Pulse generator 470, configured and constructed according to methods known to those skilled in the art, includes, for example, a hermetically sealed housing containing a power source and a controller programmed to provide dual chamber pacing, wherein hermetically sealed feedthroughs electrically couple the controller circuitry to connector contacts of a connector module attached to the housing. A functional block diagram describing an exemplary pulse generator, according to some embodiments presented below, is shown in FIG. 5F.

Figure 4B:
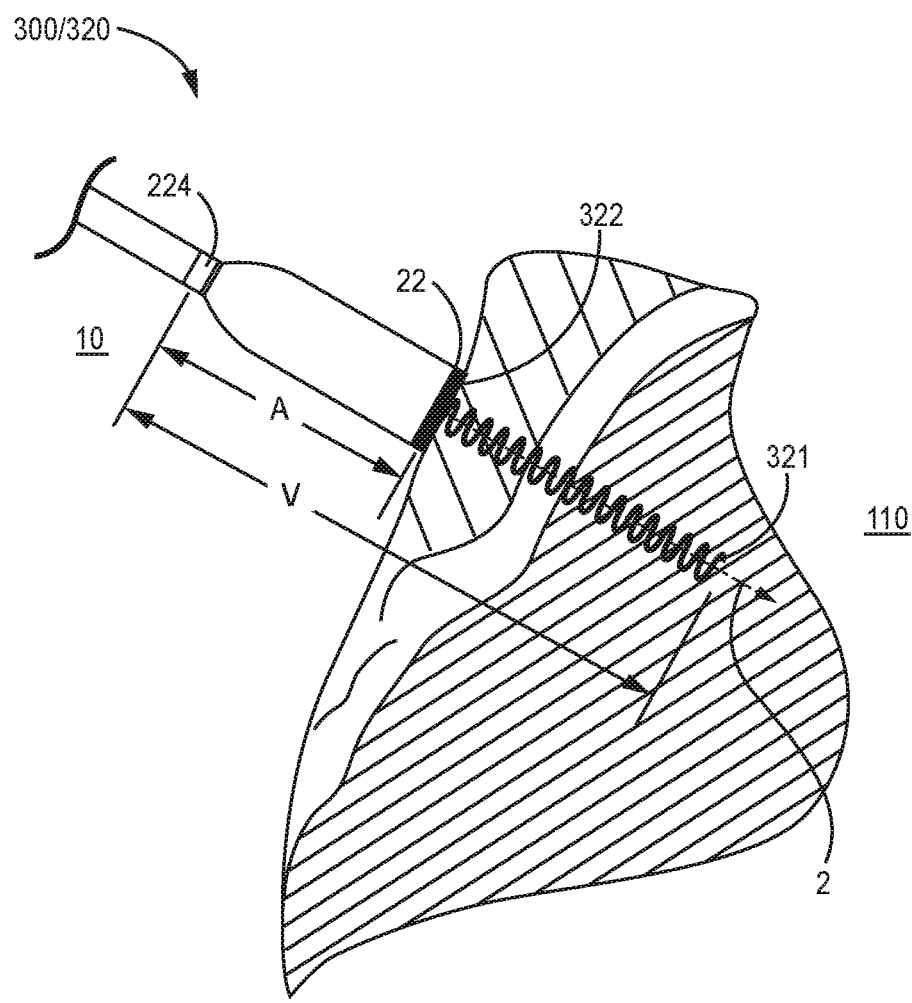
FIG. 4B is a schematic diagram showing a magnified cross-section of the septal wall in which an electrode assembly is embedded, according to some embodiments and methods.

FIG. 4B is a schematic showing a magnified cross-section of the septal wall in which lead electrode assembly 300/320 is embedded, according to some embodiments and methods, with longitudinal axis 2 extending between the RA 10 and the LV 110. FIG. 4B illustrates first cathode electrode 321 embedded within left ventricular myocardial tissue, being spaced apart from the surface of the septal wall within the LV 110, so as not to perforate through an entirety of the wall, and second cathode electrode 322 being in intimate contact with atrial myocardial tissue in the RA 10. According to some methods, as an operator engages fixation member 325 with the septal wall, a 50 Hz stimulation pulse (e.g., for 1-3 seconds) can be delivered through first cathode electrode 321 while monitoring a time between atrial and ventricular depolarization (PQ interval). If no change in the PQ interval is detected, the operator can confirm that the embedded assembly 320 circumvents tissue of the intrinsic conduction system in A-V nodal area 12 (FIG. 1A). It should be noted that, in order to prevent excessive movement of second cathode electrode 322 of the embedded assembly 320, relative to the atrial myocardial tissue, the distal length of lead 300 is constructed (e.g. coaxial construction shown in FIG. 3C), according to methods known in the art, to make the distal length in proximity to the cylindrical body significantly more flexible than the cylindrical body. FIG. 4B further illustrates lead electrode assembly 300/320 including the aforementioned optional anode electrode 224 with a spacing V between the anode electrode and the active surface of first cathode electrode 321 (e.g., in a range from about 11 mm to about 14 mm) being suitable for left ventricular pacing and sensing, and with a spacing A between the anode electrode and the active surface of second cathode electrode 322 (e.g., in a range from about 1 mm to about 8 mm) being suitable for right atrial pacing and sensing. In one or more other preferred embodiments, the spacing between the anode to the most proximal of the cathode electrodes cathode could be up to 20 mm. In some embodiments, greater or lesser spacings between the various electrodes may be desirable. According to some embodiments, a surface area of anode electrode 224, when employed by assembly 320, may be at least four times greater than the surface area of each of cathode electrodes 321, 322. As mentioned above, if the anode electrode is not included, cathode electrodes 321, 322 function in the unipolar mode, for example, using the conductive housing of pulse generator 470 as the common anode electrode, according to embodiments and methods well known to those skilled in the art.

In those applications in which the lead is employed for trans-septal pacing to stimulate both left and right branches of the Purkinje fibers to provide bi-ventricular stimulation, the fixation member (225, 325) is screwed into the ventricular septum from the right ventricle and located such that the first, distal cathode electrode (221, 321) is located within the septum to stimulate the left branch and the second, proximal cathode electrode (222, 322) is located against the septal wall to stimulate the right branch.

FIG. 5A is a plan view of an electrode assembly 520 integrated into an elongate implantable medical electrical lead 500 for an implantable medical device, according to some additional embodiments. FIG. 5A illustrates electrode assembly 520 including, like assembly 320, the substantially cylindrical body that defines longitudinal axis 2 and fixation member 325, which extends distally from the body and has first, distal-most cathode electrode 321 formed thereon. Unlike assembly 320, electrode assembly includes second and third proximal cathode electrodes 522, 523 that are formed around the substantially cylindrical body in proximity to distal end 22, being spaced apart from one another along longitudinal axis 2, wherein third cathode electrode 523 is the proximal-most cathode electrode. FIG. 5A further illustrates assembly 520 including the optional anode electrode 224, but if the anode electrode is not included, cathode electrodes 321, 522, 523 may function in the unipolar mode, for example, using the conductive housing of a pulse generator to which lead is connected (e.g., pulse generator 470) as the common anode electrode. According to the illustrated embodiment, assembly 520 is configured to be implanted within a pre-formed blind bore in the septal wall, that is a bore formed so that it does not extend all the way through the septal wall, for example, according to methods described below in conjunction with FIGS. 7A-C, and, for example, as shown in the schematic of FIG. 5D. With further reference to FIG. 5A, in an exemplary preferred embodiment of electrode assembly 520, a spacing V1 between first cathode electrode 321 and anode 224 may be about 11 mm, a spacing A2 between second, proximal cathode electrode 522 and anode electrode 224 may be about 5 mm, and a spacing A3 between third, proximal cathode electrode 523 and anode electrode 224 may be about 2 mm. Wider or narrower spacings may be desirable in some applications.

FIG. 5B is a cross-section view through section line B-B of FIG. 5A that illustrates an exemplary multi-lumen construction, which is known to those skilled in the art, of lead electrode assembly 500/520. According to the illustrated embodiment, each of elongate conductors 501-504 extends within a corresponding lumen of an elongate multi-lumen insulative body 510 (e.g., formed of extruded medical grade silicone rubber or polyurethane of a combination thereof). With reference to FIGS. 5A-B, coil conductor 501 mechanically and electrically couples (e.g. via crimping, swaging, and/or welding methods known in the art) first, distal-most electrode 321 to connector pin 25 of a proximal terminal connector 590 of lead 500, and each cable conductor 502, 503, 504 mechanically and electrically couples a corresponding electrode of second cathode electrode 522, third cathode electrode 523, and anode electrode 224, to a corresponding contact ring 26, 27, 28 of proximal terminal connector 590. FIG. 5C is a longitudinal cross-section view through electrode assembly 520 in proximity to distal end 22. FIG. 5C illustrates an insulation sleeve 52 extending around axis 2 and defining an outer diameter of the substantially cylindrical body from which fixation member 325 extends. Those skilled in the art of implantable medical lead construction will understand that coil conductor 501 extends distally out from multi-lumen insulative body 510 and into outer sleeve 52 (e.g., formed of extruded medical grade silicone rubber or polyurethane of a combination thereof), which is joined to a distal end of multi-lumen insulative body 510. FIGS. 5B-C further illustrate an inner elongate sleeve 515 (e.g., formed from a medical grade fluoropolymer) extending within conductor coil 501 to provide a passageway 508 for a stylet 680 (FIGS. 5C and 6), which, according to methods described below, facilitates the creation of the aforementioned blind bore.

The lead of FIGS. 5A-C may be employed in the same manner as the leads described above to provide atrial-synchronized left ventricular pacing or trans septal bi-ventricular pacing.

FIG. 5D illustrates electrode assembly 520 extending along the blind bore and embedded in the septal wall so that longitudinal axis 2 extends between the RA 10 and LV 110 and distal-most cathode electrode 321 is located within left ventricular myocardial tissue without perforating through to the LV 110. With reference back to FIG. 4A, the implanted lead electrode assembly 500/520 may extend from pulse generator 470, transvenously, into the RA 10 of the patient's heart as is illustrated for lead electrode assembly 200/220, 300/320. With further reference to FIG. 5D, either one of second and third cathode electrodes 522, 523 may be selected for pacing and sensing of the RA 10, depending on which is positioned at a better location in right atrial myocardial tissue, when distal-most cathode 321 has been embedded in the left ventricular myocardial tissue at a location that provides acceptable pacing and sensing of the LV 110. A flow chart shown in FIG. 5E outlines an exemplary method for using the embedded electrode assembly 520, which is as follows: per an optional step 50, an operator can confirm that the embedded assembly 520 circumvents tissue of the intrinsic conduction system in the A-V nodal area 12 (FIG. 1A) by monitoring time between atrial and ventricular depolarization (PQ interval) as a 50 Hz stimulation pulse (e.g., for 1-3 seconds) is delivered through first cathode electrode 321 while engaging fixation member 325 with the septal wall, as described above; per step 51, the operator confirms that distal-most cathode electrode 321 is located to provide acceptable pacing and sensing of the LV 110 (either unipolar or bipolar), for example, by taking EGM measurements and sending test stimulation pacing pulses via cathode electrode 321; per step 52, the operator determines which of the second and third, proximal cathode electrodes 522, 523 is better located to provide acceptable pacing and sensing of the RA 10 (either unipolar or bipolar), for example, by taking EGM measurements and sending test stimulation pacing pulses via each of electrodes 522 and 523 in sequence; and, per step 53, the operator selects one of electrodes 522 and 523 as the pace/sense electrode for the RA 10. It should be noted that the operator may be a clinician using a temporary external pulse generator, or the operator may be the pulse generator, e.g. pulse generator 470, operating according to pre-programmed instructions.

FIG. 5F is a functional block diagram generally describing components of pulse generator 470 that work in conjunction with the electrodes of the leads illustrated in FIGS. 2A-C, 3A-C and 5A-C, as described above, to provide synchronous pacing of the RA 10 and LV 110. FIG. 5F illustrates pulse generator 470 including a power source 475, processing circuitry 477, an associated memory 475 (e.g., storing pre-programmed instructions and collected data from sensing), communication circuitry 476 (e.g., telemetry), sensing and therapy generation circuitry 476, 478, and switching circuitry 472, which all function together according to means well known to those skilled in the art of dual chamber pacemaker device pulse generators. Cathode electrodes 321, 522, 523 (which may correspond to the proximal and distal cathode electrodes as illustrated in any of the above listed FIGS. 2A-C, 3A-C and 5A-C) are shown being coupled to sensing circuitry 476 and therapy generation (e.g., pacing) circuitry 478 of pulse generator 470, wherein switching circuitry 472 in conjunction with processing circuitry 477 and memory 475 may be employed to carry out steps 52 and 53 described above. Furthermore, processing circuitry 477 may be programmed to lengthen refractory periods for both right atrial and left ventricular sensing, during which periods sensed depolarization events do not impact a pacing rate, which rate is also controlled by processing circuitry 477. In preferred embodiments employing atrial-synchronized left ventricular pacing, electrode 522 is employed to both pace and sense the atrium, e.g, in conjunction with delivery of DDD pacing. However, in some alternative embodiments, electrode 522 may be employed only to sense atrial depolarizations, e.g., in conjunction with delivery of VDD pacing.

In the event that the pulse generator is adapted to provide bi-ventricular pacing wherein the first, distal cathode 321 is situated to stimulate the left branch of the Purkinje fiber system and a second, proximal cathode 522 is situated to stimulate the right branch of the Purkinje fiber system, therapy generation circuitry 478 is correspondingly configured to deliver ventricular pacing pulses to these first and second cathode electrodes. In such embodiments, sensing circuitry 476 may be employed to sense depolarizations using one or both of electrodes 321 and 522.

Figure 6:
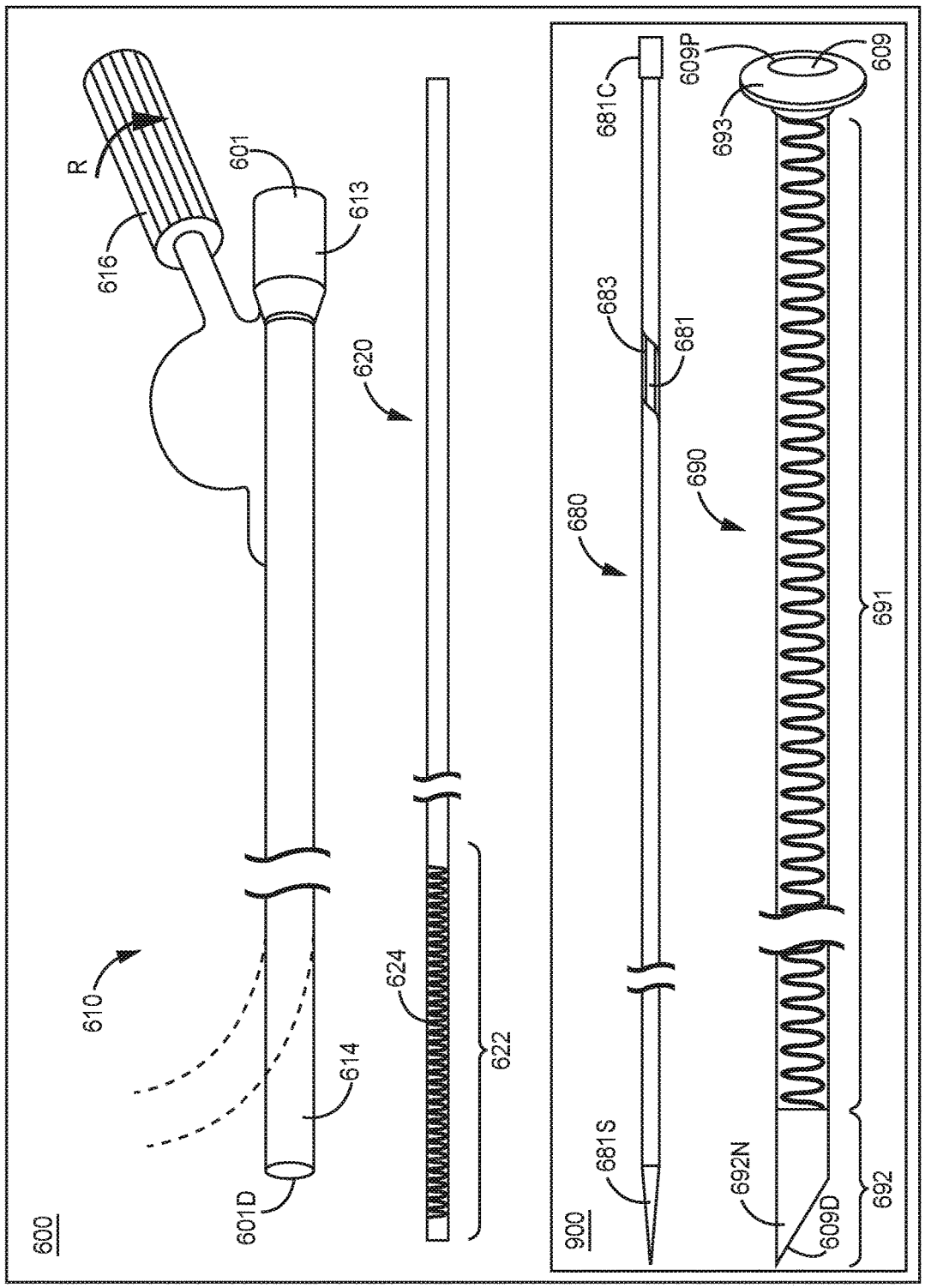
FIG. 6 is a plan view of an interventional delivery system, according to some embodiments, that may be used to implant a lead electrode assembly as described in conjunction with the schematics of FIGS. 7A-7D.

FIG. 6 is a plan view of an interventional delivery system 600, according to some embodiments, which may be used to implant lead electrode assembly 500/520, for example, as described below in conjunction with the schematics of FIGS. 7A-D. FIG. 6 illustrates delivery system 600 including a delivery catheter 610, a reference catheter 620, and a boring assembly 900. Boring assembly 900 is shown including the aforementioned stylet 680 and a tubular member 690. A cut-away section of FIG. 6 shows stylet 680 including a conductive core 681, which may be an elongate wire formed from a medical grade stainless steel having a nominal diameter between about 0.014 inch and 0.020 inch in some embodiments. The cut-away section further shows an insulative jacket 683, for example, being formed from a medical grade fluoropolymer, that extends around a length of core 681 between a proximal terminal contact 681C and a sharp distal tip 681S of stylet core 681. According to the illustrated embodiment, boring assembly 900 is used by inserting stylet 680 into a lumen 609 of tubular member 690. Stylet 680 is inserted into lumen 609 so that sharp distal tip 681S of stylet 680 is located in proximity to a needle tip 692N of a rigid distal segment 692 of tubular member 690, and so that proximal terminal contact 681C of stylet 680 protrudes from a proximal opening 609P of tubular member lumen 609, for example, so that electrical measurements may be made as described below. Tubular member lumen proximal opening 609P is shown being formed by a knob 693 of tubular member 690. FIG. 6 further illustrates delivery catheter 610 having a lumen 601, which extends from a proximal opening formed by a hub 613 of catheter 610 to a distal opening 601D, and which is sized to receive passage of rigid distal segment 692 and a flexible proximal segment 691 of tubular member 690 therethrough, for the operation of the boring assembly according to methods described below. Flexible proximal segment 691 of tubular member 690 is constructed to be pushable as well as flexible for the operation of boring assembly 900, for example, proximal segment 691 may be formed from a wire reinforced medical grade polymer (e.g. a close wound stainless steel coil embedded in an appropriate grade of PEBAX polymer). Delivery catheter 610 may be a steerable type having a construction that is well known in the art, for example, like that of the Medtronic Attain™ Deflectable catheter or the Model C304 Medtronic SelectSite® Deflectable Catheter Delivery System, in which rotation of a control member 616, per arrow R, causes a distal tip 614 of catheter 610 to deflect, for example, according to the dashed lines in FIG. 6.

Figure 7B:
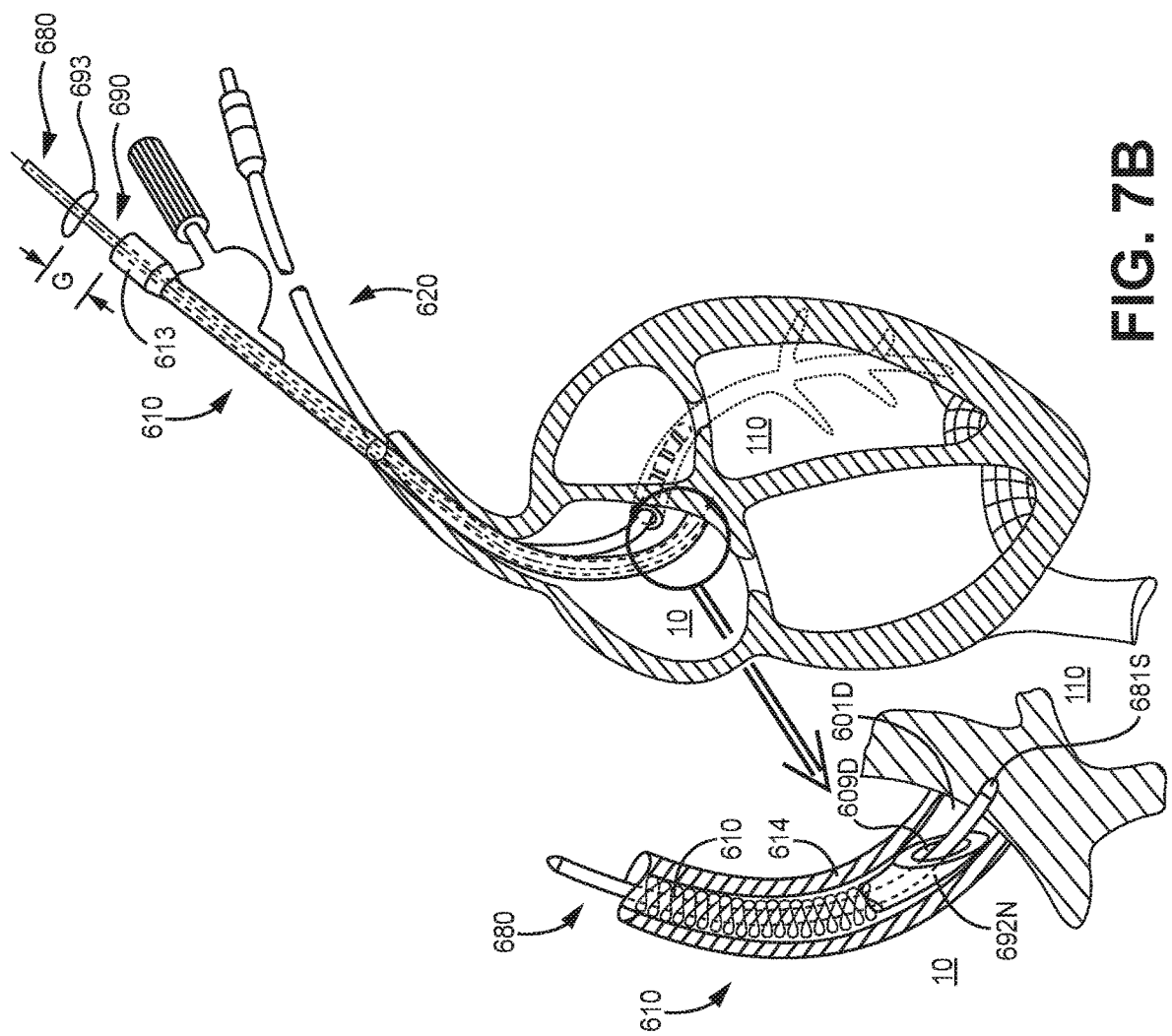
FIG. 7B is a schematic diagram that depicts a subsequent step, according to some methods, in which a distal tip of a delivery catheter is positioned within the RA.
Figure 7A:
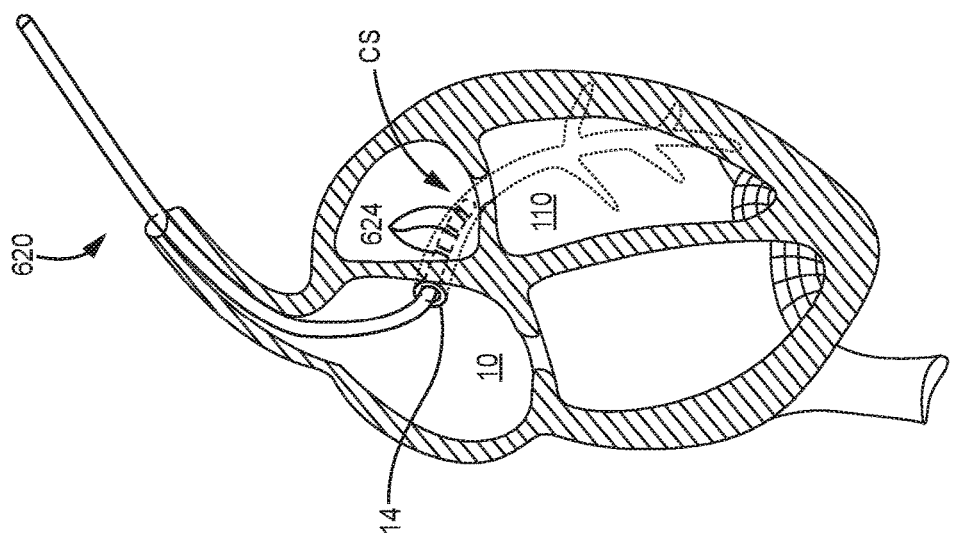
FIG. 7A is a schematic diagram that depicts an initial step for implanting an electrode assembly, according to some methods, in which a reference catheter of a delivery system is fitted within the coronary sinus (CS) of a patient's heart.

With further reference to FIG. 6, reference catheter 620 of delivery system 600 includes an elongate distal portion 622 which is sized to fit within the CS of a patient's heart, having been passed into the CS via ostium 14, as illustrated in FIG. 7A. In FIG. 6, one embodiment of reference catheter 620 is shown including a radiopaque marker 624 in the form of a coil that extends along a length of distal portion 622. In an alternate embodiment of reference catheter 620, radiopaque marker 624 may be in the form of multiple radiopaque bands spaced apart from one another along distal portion 622, for example, as shown in FIGS. 7A-D. In either case, radiopaque marker 624 of reference catheter distal portion 622, when extending within the CS, can provide a fluoroscopic visual reference to assist an operator in positioning delivery catheter distal tip 614 at the desired location along the RA septal wall, and in properly orienting distal tip 614 at an appropriate angle that generally corresponds to the extent of the radiopaque marker 624 in the CS, for example, according to the arrow of FIG. 7A, and as described above in conjunction with FIGS. 1A-B. According to some methods, delivery catheter 610 may be used to deliver reference catheter 620 to the CS. Construction methods known in the art of medical electrical leads may be used to form reference catheter 620 for example, employing any suitable medical grade polymer tubing and any suitable medical grade radiopaque material known in the art.

With reference to FIG. 7B, after the operator, by using radiopaque marker(s) 624 of reference catheter 620 for a fluoroscopic visual reference, has positioned catheter distal tip 614 within RA 10, so that catheter lumen distal opening 601D is against the septal wall at a location between CS ostium 14 and A-V nodal area 12 (FIG. 1A), and so that distal tip is generally directed toward the LV 110, the operator can advance the boring assembly through delivery catheter 610. FIG. 7B illustrates tubular member 690 of the boring assembly having been advanced within catheter lumen 601 until needle tip 692N is in close proximity to catheter lumen distal opening 601D. FIG. 7B further illustrates stylet 680 of the boring assembly having been advanced within tubular member lumen 609 until stylet sharp tip 681S protrudes distally therefrom.

Figure 8:
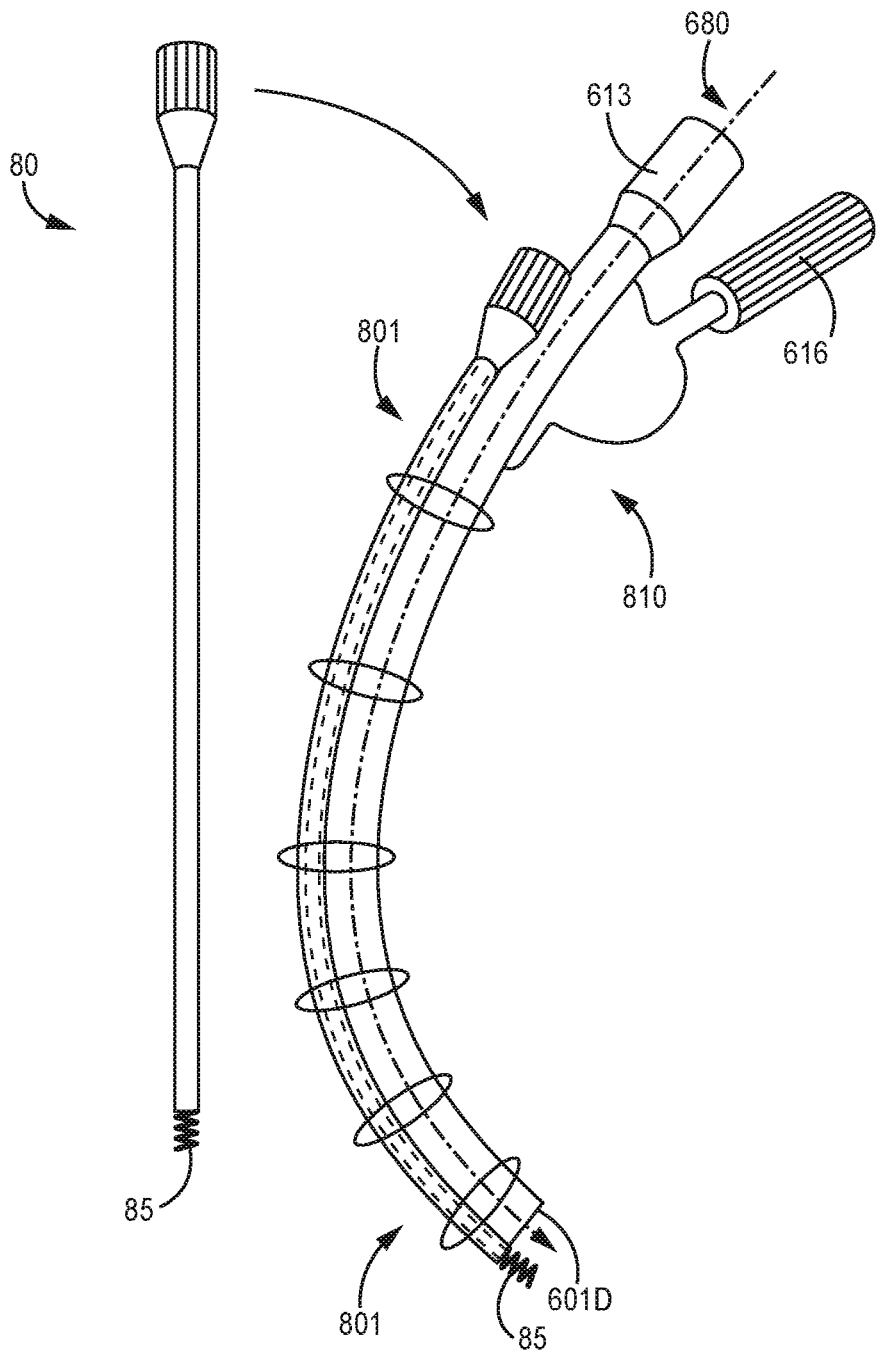
FIG. 8 illustrates an alternate embodiment of an interventional delivery system.

According to some methods, the operator may grip knob 693 to advance tubular member 690 within catheter lumen 601 until some slight resistance is felt, indicating that needle tip 692N is near the septal wall, as shown in FIG. 7B The operator then inserts sharp tip 681S of stylet conductive core 681 into the septal wall, as is also shown in FIG. 7B, by advancing stylet 680 through tubular member lumen 609 and out distal opening 609D thereof. Prior to inserting sharp tip 681S, the operator may make superficial contact with the septal wall, without piercing into the wall, to take electrical measurements, via electrical connection to proximal terminal contact 681C of stylet conductive core 680 and verify the location for creating the blind bore. Once the location is verified, having measured a clear atrial signal (P-wave) and a clear far-field ventricular signal (R-wave), and as the operator inserts sharp tip 681S into the septal wall, for example, up to about 2 millimeters depth, the operator may continue to take electrical measurements. According to some alternate embodiments and/or methods, a delivery catheter 810 in conjunction with an elongate fixation tool 80, which are shown in FIG. 8, may be employed in lieu of delivery catheter 610 in system 600. FIG. 8 illustrates delivery catheter 810, like catheter 610, including hub 613, lumen 601 and control member 616, but further including an open-ended conduit 801 that extends alongside lumen 601. According to some embodiments, catheter 810 may be constructed in a similar fashion to the Medtronic Attain™ Command Catheter. FIG. 8 further illustrates fixation tool 80 being sized for passage through conduit 801 and including a fixation member 85 (e.g., a helix wire), which terminates a distal end thereof and is configured to pierce myocardial tissue. According to the illustrated alternate embodiment, when delivery catheter 810 is positioned in the RA 10 like catheter 610 (FIG. 7B), fixation member 85, having been passed through conduit 801 and positioned alongside distal opening 601D of catheter lumen 601, can be engaged with the atrial myocardial tissue by rotating tool around a longitudinal axis thereof to secure catheter distal opening 601D in place during subsequent steps of the implant process, for example, as describe below.

With reference to FIG. 7C, after inserting stylet tip 681S, the operator advances, for a predetermined distance, tubular member 690 over stylet 680 so that distal segment needle tip 692N tubular member 690 enters the septal wall and creates a blind bore extending from right atrial myocardial tissue to left ventricular myocardial tissue. According to preferred embodiments and method, the predetermined distance, over which needle tip 692N is advanced, is controlled, or dictated by confronting engagement of tubular member knob 693 with delivery catheter hub 613, as shown in FIG. 7C. With reference back to FIG. 7B a gap G between knob 693 and hub 613 corresponds to the controlled depth and may be from about 3 mm to 5 mm. After forming the blind bore with needle tip 692N, the operator may retract tubular member 690 out from catheter 610, while leaving stylet 680 in place. Then, with reference to FIG. 7D, the operator can advance lead electrode assembly 500/520 over stylet 680 and into the pre-formed bore until distal-most cathode electrode 321 (formed at the distal end of fixation member 325) comes into contact with the end of the bore. With reference back to FIG. 5C, which shows stylet 680 extending within passageway 508 of lead electrode assembly 500/520, according to some embodiments, passageway 508 is terminated at a distal end thereof by a seal member 58 (e.g. formed from medical grade silicone rubber). According to the illustrated embodiment, seal member 58 allows stylet tip 681S to pass through but prevents a backflow of blood into passageway. Suitable constructions for seal member 58 are known to those skilled in the art. According to an exemplary embodiment, a diameter of tubular member distal segment 692 is such to create a bore having a diameter from about 1 mm to about 1.5 mm, which is then stretched, for example, up to about 130%, as lead electrode assembly 500/520 is advanced therein. To secure lead electrode assembly 500/520 to the septal wall, the operator engages myocardial tissue at the end of the bore with fixation member 325 by rotating lead electrode assembly 500/520 around longitudinal axis 2 which advances distal-most cathode electrode 321 deeper into ventricular myocardial tissue (e.g., over a distance of about 6 to 6 mm) without perforating through to the RV 110, as shown in FIG. 7D. Then stylet 680 and catheter 610 can be withdrawn from the patient's body.

Finally, as alluded to above, either of delivery catheters 610, 810 described above may be used in conjunction with reference catheter 620, either with or without the boring assembly, to deliver other embodiments of lead electrode assemblies (e.g. assemblies 200/220, 300/320) described herein to the implant site. Furthermore, interventional delivery systems described herein may employ constructions and components adapted from those described in the publicly available Medtronic Cardiac Leads and Delivery Systems Product Catalog, which is hereby incorporated by reference.

In the foregoing detailed description, the invention has been described with reference to specific embodiments. However, it may be appreciated that various modifications and changes can be made without departing from the scope of the invention as set forth in the appended claims; and, for example, in various combinations of elements and method steps described above according to the following statements that provide a summary of embodiments and methods.

1. An electrode assembly for an implantable medical device comprising:
   a substantially cylindrical body defining a longitudinal axis of the assembly;
   a fixation member extending distally from a distal end of the body and being configured to pierce into a septal wall of a patient's heart and to secure the assembly to the septal wall;
   a first cathode electrode formed on the fixation member;
   a second cathode electrode formed on a distal end of the body; and
   an elongate lead comprising a distal length, from which the substantially cylindrical body extends, a proximal connector, and an assembly of insulated conductors extending therebetween, each conductor coupling a contact of the terminal connector to a corresponding electrode, and the terminal connector being configured for connection to a pulse generator of the medical device, the pulse generator being configured to deliver cardiac pacing pulses through the electrodes; and
   wherein an entirety of the second cathode electrode extends within an inner perimeter of the fixation member, or the entirety of second cathode electrode extends around an outer perimeter of the fixation member.

2. The assembly of statement 1, wherein a length of the fixation member is at least 5 mm and no more than 15 mm or no longer than 20 mm, the length being defined from the distal end of the body to a distal tip of the fixation member.

3. The assembly of statement 1 or 2, further comprising a third cathode electrode mounted around the substantially cylindrical body.

4. The assembly of any one of statements 1-3, further comprising an anode electrode mounted around the distal length of the lead and being located proximal to a proximal-most cathode of the cathode electrodes.

5. The assembly of statement 4, wherein the anode electrode is spaced apart from the proximal-most cathode of the cathode electrodes by no more than 8 mm or no longer than 20 mm.

6. The assembly of statement 4 or 5, wherein a surface area of the anode electrode is at least four times greater than a surface area of each cathode electrode.

7. A method for using the assembly of statement 3 to provide synchronous pacing stimulation to a right atrium and a left ventricle of a patient's heart when the assembly is embedded within a septal wall of the heart so that the longitudinal axis thereof extends between the right atrium and the left ventricle and the distal-most cathode electrode is located entirely within left ventricular myocardial tissue of the septal wall to provide acceptable pacing and sensing of the left ventricle; the method comprising determining which of the second and third cathode electrodes is better located, being in contact with atrial myocardial tissue, to provide acceptable pacing and sensing of the right atrium.

8. The method of statement 7, further comprising confirming that the embedded assembly has circumvented A-V nodal tissue.

9. An implantable medical device comprising the electrode assembly of any of statements 1-6.

10. An interventional delivery system comprising a delivery catheter having a lumen sized for passage of an electrode assembly of an implantable medical device therethrough for implant in a patient's heart, the passage from a proximal opening of the catheter lumen, formed by a hub of the catheter, to a distal opening of the catheter lumen; and the system further comprising:
a reference catheter having a distal portion sized to fit within a coronary sinus of the patient's heart, the reference catheter including one or more radiopaque elements located along a length of the distal portion; and
a boring assembly comprising:
a stylet comprising an elongate conductive core, and an insulative jacket, the conductive core including a proximal terminal contact and a sharp distal tip, the insulative jacket extending around an entire length of the conductive core except for the proximal terminal contact and the sharp distal tip; and
a tubular member defining an elongate lumen and comprising a proximal knob, a flexible proximal segment extending distally from the knob, a rigid distal segment extending distally from the proximal segment, and a piercing needle tip terminating the rigid distal segment, the lumen of the member including a proximal opening formed by the knob and a distal opening formed by the needle tip of the distal segment, the lumen of the member being sized to receive therethrough passage of the stylet so that the sharp distal tip of the stylet can extend distally out from the distal opening of the member lumen, and the tubular member being sized for passage through the lumen of the delivery catheter, the passage of the tubular member being stopped by confronting engagement of the knob against the catheter hub; and
wherein the length of the tubular member, from the knob to the piercing needle tip is from 3 mm to 5 mm greater than an overall length of the catheter.
11. The system of statement 10, wherein the delivery catheter has an open-ended conduit extending alongside the lumen of the catheter, a distal opening of the conduit being located in proximity to the distal opening of the catheter lumen; and the system further comprises an elongate fixation tool having a fixation member terminating a distal end thereof, the fixation tool being sized for passage through the conduit of the catheter and out the distal opening thereof so that the fixation member of the tool can be positioned adjacent to the distal opening of the catheter lumen.
12. A kit comprising the electrode assembly of any of statements 1-6, or the implantable medical device of claim 9, and the interventional delivery system of statement 10 or 11.
13. A method for implanting an electrode assembly of an implantable medical device in a patient's heart, the method comprising:
positioning one or more radiopaque markers in a coronary sinus of the patient's heart;
positioning, by using the one or more positioned radiopaque markers as a fluoroscopic visual reference, a distal tip of a delivery catheter within a right atrium of the patient's heart so that a distal opening of a lumen of the catheter is against a septal wall of the heart at a location between the ostium of the coronary sinus and the A-V nodal area of the right atrium, and so that the tip of the catheter is generally directed toward a left ventricle of the patient's heart; and advancing the electrode assembly through the lumen of the catheter and into the septal wall.
14. The method of statement 13, further comprising creating a blind bore within the septal wall by passing a boring assembly out through the distal opening of the positioned delivery catheter before advancing the electrode assembly; and wherein the electrode assembly is advanced into the blind bore.
15. The method of statement 14, wherein creating the blind bore comprises:
inserting a sharp distal tip of a stylet of the boring assembly into the septal wall;
advancing, over a predetermined distance, a needle tip of a tubular member of the boring assembly over the inserted sharp distal tip of the boring assembly stylet, the predetermined distance extending from right atrial tissue of the septal wall to left ventricular tissue of the septal wall;
retracting the tubular member needle tip from the septal wall while leaving the inserted stylet sharp tip in place; and
advancing the electrode assembly over the inserted boring assembly stylet and into the blind bore.
16. The method of statement 15, further comprising taking electrical measurements via the sharp tip of the boring assembly stylet before inserting the sharp tip into the septal wall.
17. The method of statement 15 or 16, wherein the predetermined distance for advancing the needle tip of a boring assembly tubular member is dictated by confronting engagement of a proximal knob of the tubular member against a hub of the delivery catheter.
18. The method of any of statements 14-17, further comprising rotating the electrode assembly to engage a fixation member thereof, after advancing the electrode assembly into the blind bore.
19. The method of any of statements 13-18, further comprising securing the distal opening of the lumen of the positioned catheter against the septal wall.
20. The method of statement 19, wherein securing the distal opening of the lumen of the positioned catheter comprises:
passing an elongate fixation tool through a conduit of the positioned catheter until a fixation member of the tool is positioned alongside the distal opening of the catheter lumen; and
engaging the positioned fixation member of the tool with the septal wall by rotating the fixation tool around a longitudinal axis thereof.
21. An electrode assembly for an implantable medical device that delivers synchronous atrioventricular cardiac pacing, the assembly comprising:
a substantially cylindrical body defining a longitudinal axis of the assembly;
so a fixation member extending distally from a distal end of the body and being configures to pierce into a septal wall of a patient's heart and to secure the assembly to the septal wall;
a first cathode electrode formed on the fixation member and being located to stimulate left ventricular myocardial tissue when the fixation member secures the assembly to the septal wall;
a second cathode formed on a distal end of the body and being located to stimulate right atrial myocardial tissue when the fixation member secures the assembly to the septal wall; and an elongate lead comprising a distal length, from which the substantially cylindrical body extends, a proximal terminal connector, and an assembly of insulated conductors extending therebetween, each conductor coupling a contact of the terminal connector to a corresponding electrode, and the terminal connector being configured for connection to a pulse generator of the medical device, the pulse generator being configured to deliver cardiac pacing pulses through the electrodes; and wherein an entirety of the second cathode electrode extends within an inner perimeter of the fixation member, or the entirety of second cathode electrode extends around an outer perimeter of the fixation member.

22. The assembly of statement 21, wherein the fixation member is in the form of a helix that extends distally from the distal end and has an insulative coating or jacket electrically isolating first cathode electrode from second cathode electrode.

23. The assembly of statement 21 or 22, wherein a flexibility of the distal length of the elongate lead in proximity to the cylindrical body is significantly less than a flexibility of the cylindrical body.

24. A cardiac stimulation device, comprising:
an cylindrical body comprising a distal end;
a fixation member extending distally from the distal end of the cylindrical body and being configured to pierce into a Triangle of Koch region of a patient's heart and to secure the assembly to the septal wall;
a first cathode electrode formed on the fixation member;
a second cathode electrode formed on the distal end of the cylindrical body, wherein an entirety of the second cathode electrode extends within an inner perimeter of the fixation member, or the entirety of second cathode electrode extends around an outer perimeter of the fixation member; and
a pulse generator coupled to the first and second cathode electrodes and configured to deliver atrial ventricular or biventricular septal cardiac pacing pulses thereto.

25. The device of statement 24, wherein a length of the fixation member is at least 5 mm and no more than 8 mm, the length being defined from the distal end of the cylindrical body to a distal tip of the fixation member.

26. The device of statement 25, further comprising a third cathode electrode mounted around the substantially cylindrical body.

27. The lead of statement 26, further comprising an anode electrode mounted around the cylindrical body and being located proximal to the first, second and third cathode electrodes.

28. The lead of statement 25, further comprising an anode electrode mounted around the cylindrical and being located proximal to the first and second cathode electrodes.

29. A cardiac stimulation system, comprising
an elongate lead body comprising a distal end, a proximal terminal connector and an assembly of insulated conductors extending therebetween;
a fixation member extending distally from the distal end of the lead body and being configured to pierce into a septal wall of a patient's heart and to secure the assembly to the septal wall;
a first cathode electrode formed on the fixation member; and a second cathode electrode formed on the distal end of the lead body, wherein an entirety of the second cathode electrode extends within an inner perimeter of the fixation member, or the entirety of second cathode electrode extends around an outer perimeter of the fixation member; and
a pulse generator coupled to the terminal connector and configured to deliver atrial synchronized ventricular or biventricular septal cardiac pacing pulses to the first and second cathode electrodes.

30. The system of statement 29, wherein a length of the fixation member is at least 5 mm and no more than 8 mm, the length being defined from the distal end of the lead body to a distal tip of the fixation member.

31. The system of statement 30, further comprising a third cathode electrode mounted around the lead body.

32. The system of statement 31, further comprising an anode electrode mounted around the lead body and being located proximal to the first, second and third cathode electrodes.

33. The system of statement 32, further comprising an anode electrode mounted around the distal length of the lead and being located proximal to the first and second cathode electrodes.

34. A cardiac stimulation lead, comprising:
an elongate lead body comprising a distal end, a proximal terminal connector and an assembly of insulated conductors extending therebetween;
a fixation member extending distally from the distal end of the lead body and being configured to pierce into a septal wall of a patient's heart and to secure the assembly to the septal wall;
a first cathode electrode formed on the fixation member and coupled to one of the insulated conductors;
a second cathode electrode formed on the distal end of the lead body and coupled to one of the insulated conductors, wherein an entirety of the second cathode electrode extends within an inner perimeter of the fixation member, or the entirety of second cathode electrode extends around an outer perimeter of the fixation member.

35. The lead of statement 34, wherein a length of the fixation member is at least 5 mm and no more than 8 mm, the length being defined from the distal end of the lead body to a distal tip of the fixation member.

36. The lead of statement 35, further comprising a third cathode electrode mounted around the lead body.

37. The lead of statement 36, further comprising an anode electrode mounted around the lead body and being located proximal to the first, second and third cathode electrodes.

38. The lead of statement 37, further comprising an anode electrode mounted around the lead body and being located proximal to the first and second cathode electrodes.

In conjunction with the above disclosure, we claim:
1. A cardiac stimulation system, comprising:
an elongate lead body comprising a flexible distal portion and a distal end, a proximal terminal connector and an assembly of insulated conductors extending therebetween;
a fixation member extending distally from the distal end of the elongate lead body and being configured to pierce into a septal wall of a patient's heart and to secure the elongate lead body to the septal wall;
a first cathode electrode formed on the fixation member;

a second cathode electrode formed on the distal end of the lead body, wherein an entirety of the second cathode electrode extends within an inner perimeter of the fixation member, and wherein the second cathode electrode forms a non-piercing active face configured to maintain active external contact with a corresponding outer surface area of the septal wall within the inner perimeter of the fixation member when the fixation member secures the elongate lead body to the septal wall; and a pulse generator coupled to the terminal connector and configured to deliver cardiac pacing pulses to the first and second cathode electrodes.

2. The system of claim 1, wherein a length of the fixation member is at least 5 mm and no more than 20 mm, the length being defined from the distal end of the elongate lead body to a distal tip of the fixation member.

3. The system of claim 1, further comprising an anode electrode mounted around a distal length of the elongate lead body and being located proximal to the first and second cathode electrodes.

4. The system of claim 1, wherein the pulse generator is configured to deliver atrial synchronized left ventricular pacing via the first and second cathode electrodes.

5. The system of claim 1, wherein the pulse generator is configured to deliver bi-ventricular pacing via the first and second cathode electrodes.

6. A cardiac stimulation device, comprising:
a cylindrical body comprising a flexible distal portion and a distal end;
a fixation member extending distally from the distal end of the cylindrical body and being configured to pierce into a septal wall of a patient's heart and to secure the device to the septal wall;
a first cathode electrode formed on the fixation member;
a second cathode electrode formed on the distal end of the cylindrical body, wherein an entirety of the second cathode electrode extends within an inner perimeter of the fixation member, and wherein the second cathode electrode forms a non-piercing active face configured to maintain active external contact with a corresponding outer surface area of the septal wall within the inner perimeter of the fixation member when the fixation member secures the device to the septal wall; and
a pulse generator coupled to the first and second cathode electrodes and configured to deliver negatively charged cardiac pacing pulses to the first and second cathode electrodes.

7. The device of claim 6, wherein the pulse generator is configured to deliver atrial synchronized left ventricular pacing via the first and second cathode electrodes.

8. The device of claim 6, wherein the pulse generator is configured to deliver bi-ventricular pacing via the first and second cathode electrodes.

* * * * *